(12) United States Patent
Kuhn

(10) Patent No.: US 10,080,499 B2
(45) Date of Patent: Sep. 25, 2018

(54) IMPLANTABLE MEDICAL SYSTEM INCLUDING MULTIPLE SENSING MODULES

(75) Inventor: Jonathan L. Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 3052 days.

(21) Appl. No.: 12/182,484

(22) Filed: Jul. 30, 2008

(65) Prior Publication Data

US 2010/0030043 A1 Feb. 4, 2010

(51) Int. Cl.
| | |
|---|---|
| *A61B 5/1459* | (2006.01) |
| *A61B 5/01* | (2006.01) |
| *A61B 5/0215* | (2006.01) |
| *A61B 5/11* | (2006.01) |
| *A61B 5/00* | (2006.01) |
| *A61B 5/145* | (2006.01) |

(Continued)

(52) U.S. Cl.
CPC .......... *A61B 5/0086* (2013.01); *A61B 5/0031* (2013.01); *A61B 5/14542* (2013.01); *A61B 5/0205* (2013.01); *A61B 5/1459* (2013.01); *A61N 1/3655* (2013.01); *A61N 1/36542* (2013.01); *A61N 1/36557* (2013.01); *A61N 1/36564* (2013.01); *A61N 1/36578* (2013.01)

(58) Field of Classification Search
CPC . A61B 5/0086; A61B 5/0031; A61B 5/14542; A61B 5/1459; A61B 5/0205; A61N 1/36578; A61N 1/36564; A61N 1/36557; A61N 1/3655; A61N 1/36542

USPC .............. 600/309–310, 322–323, 325, 327, 600/332–333, 339, 341
See application file for complete search history.

(56) References Cited

U.S. PATENT DOCUMENTS

| | | | | |
|---|---|---|---|---|
| 4,476,870 | A | * | 10/1984 | Peterson et al. .............. 600/312 |
| 4,517,456 | A | * | 5/1985 | Halsall et al. ................ 250/226 |
| 4,543,961 | A | * | 10/1985 | Brown .......................... 600/480 |

(Continued)

FOREIGN PATENT DOCUMENTS

| | | |
|---|---|---|
| WO | WO98/38907 A | 9/1998 |
| WO | WO 98/38907 A1 | 9/1998 |

(Continued)

OTHER PUBLICATIONS

International Search Report, PCT/US2008/009197, dated Feb. 2, 2009, 7 pages.

(Continued)

*Primary Examiner* — Rene Towa

(57) ABSTRACT

A medical system includes at least two sensing modules that each generate an optical signal that changes as a function of a physiological parameter of a patient. The sensing modules may be coupled to a common light source and a common receiver via an optically transmissive member. At least a first sensing module that is closest to the light source along a length of the optically transmissive member may include a waveguide to split the light emitted by the light source. A first portion of the light may be directed toward the first sensing module and a second portion of the light may be directed toward a second sensing module that is placed downstream of the first sensing module in a direction substantially along the direction of light flow through the optically transmissive member and away from the light source.

26 Claims, 14 Drawing Sheets

(51) Int. Cl.
*A61B 5/0205* (2006.01)
*A61N 1/365* (2006.01)

(56) References Cited

U.S. PATENT DOCUMENTS

| | | | |
|---|---|---|---|
| 4,649,529 A | 3/1987 | Avicola | |
| 4,730,622 A * | 3/1988 | Cohen | 600/480 |
| 4,735,212 A * | 4/1988 | Cohen | 600/480 |
| 5,089,697 A * | 2/1992 | Prohaska | 250/227.21 |
| 5,451,772 A | 9/1995 | Narendran | |
| 5,698,848 A | 12/1997 | Belk | |
| 6,175,108 B1 | 1/2001 | Jones et al. | |
| 6,216,022 B1 | 4/2001 | Tyrrell et al. | |
| 7,224,465 B2 | 5/2007 | Balachandran et al. | |
| 7,260,283 B2 | 8/2007 | Lieberman et al. | |
| 2002/0133211 A1 * | 9/2002 | Weiner et al. | 607/61 |
| 2002/0133216 A1 | 9/2002 | Connelly et al. | |
| 2002/0159671 A1 | 10/2002 | Boyd et al. | |
| 2002/0196995 A1 * | 12/2002 | Kersey et al. | 385/13 |
| 2003/0231818 A1 * | 12/2003 | Cantin et al. | 385/12 |
| 2004/0244502 A1 * | 12/2004 | Youngner et al. | 73/862.59 |
| 2004/0247223 A1 | 12/2004 | Tietjen | |
| 2006/0247724 A1 | 11/2006 | Gerber et al. | |
| 2007/0201031 A1 * | 8/2007 | Axelrod et al. | 356/477 |
| 2007/0280581 A1 * | 12/2007 | Wipiejewski | 385/12 |
| 2008/0085074 A1 | 4/2008 | Wakahara et al. | |
| 2008/0255629 A1 * | 10/2008 | Jenson et al. | 607/19 |
| 2009/0185772 A1 * | 7/2009 | Xia et al. | 385/13 |

FOREIGN PATENT DOCUMENTS

| | | |
|---|---|---|
| WO | WO2007/096874 A | 8/2007 |
| WO | WO 2007/096874 A2 | 8/2007 |
| WO | WO2007/099531 A | 9/2007 |
| WO | WO 2007/099531 A2 | 9/2007 |
| WO | WO2007/137037 A | 11/2007 |
| WO | WO 2007/137037 A1 | 11/2007 |

OTHER PUBLICATIONS

International Search Report and Written Opinion from corresponding PCT Application Serial No. PCT/US2008/009197 dated Feb. 2, 2009 (14 pages).
Response to Written Opinion from corresponding PCT Application Serial No. PCT/US2008/009197 dated Feb. 2, 2009 (20 pages).
International Preliminary Report on Patentability from corresponding PCT Application Serial No. PCT/US2008/009197 dated Oct. 25, 2010 (12 pages).

* cited by examiner

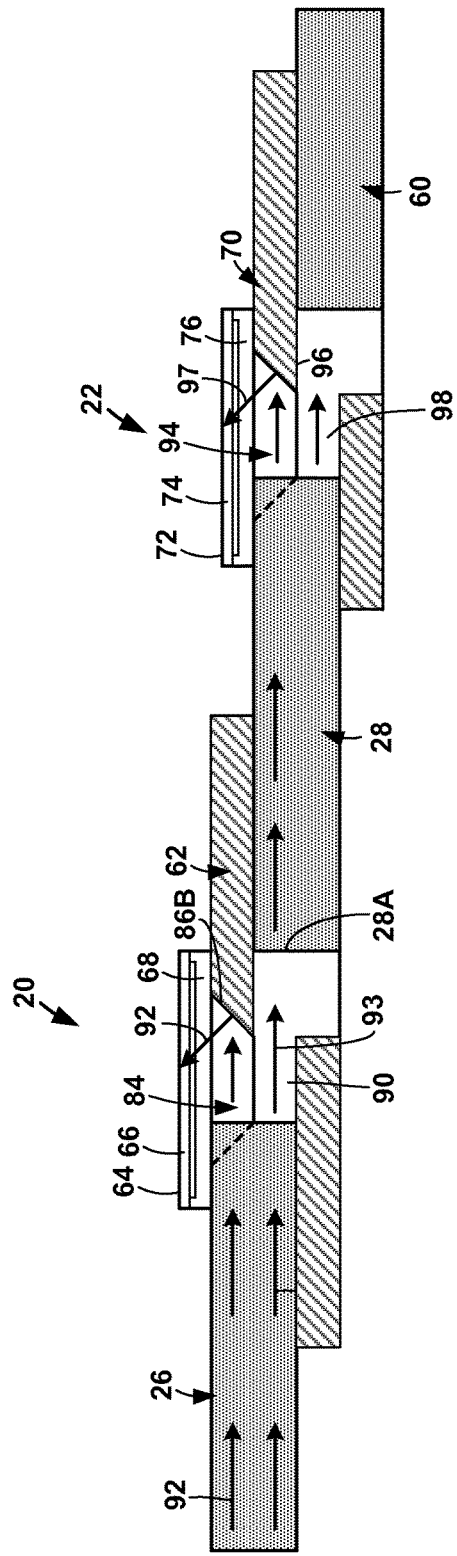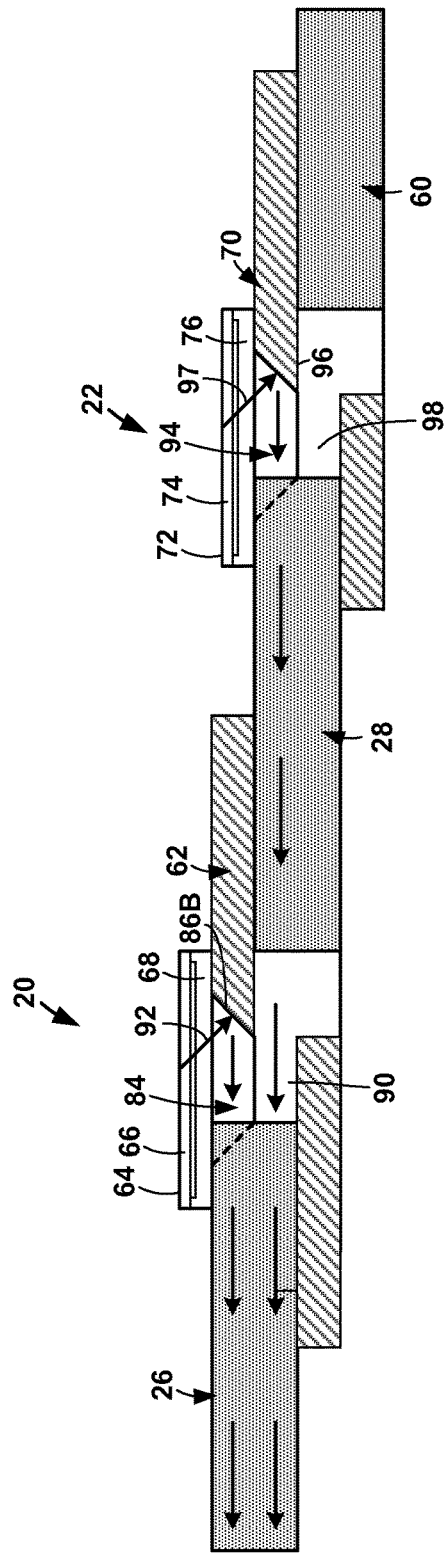
FIG. 6A
FIG. 6B

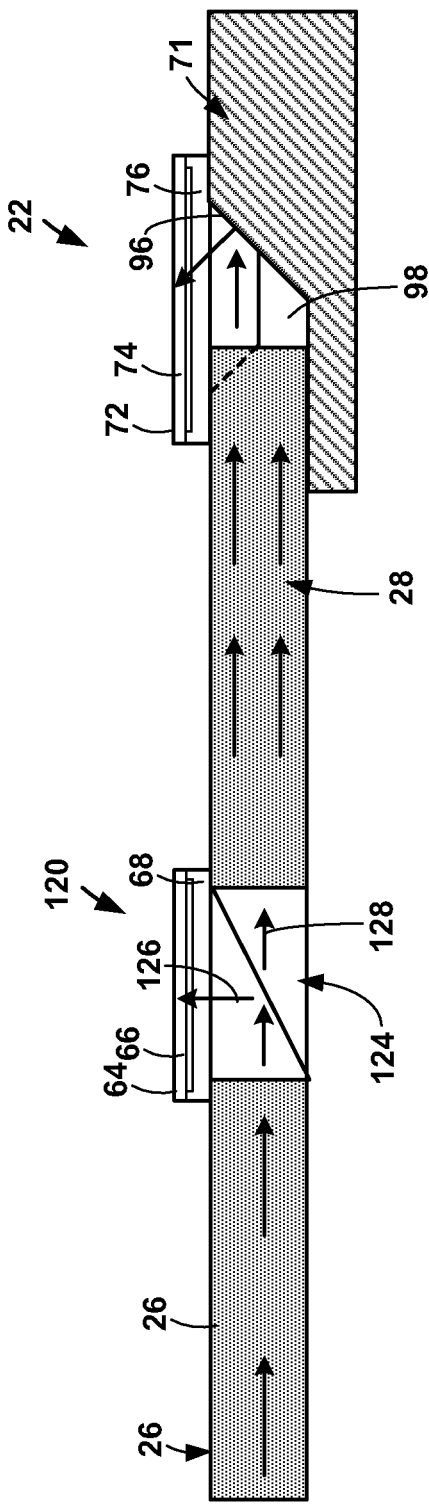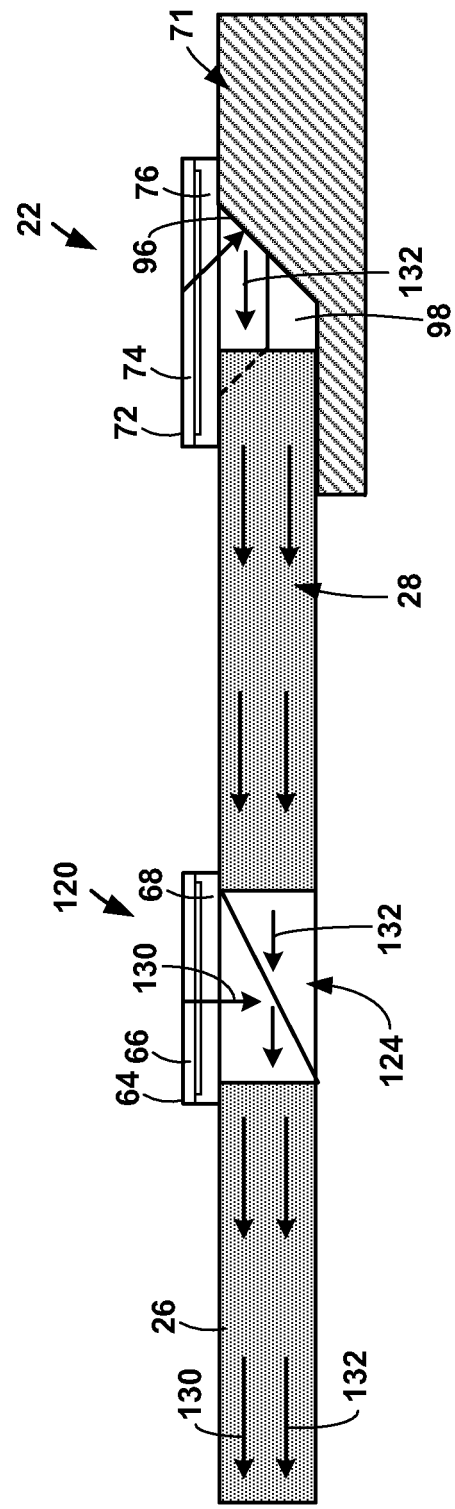
FIG. 8A
FIG. 8B

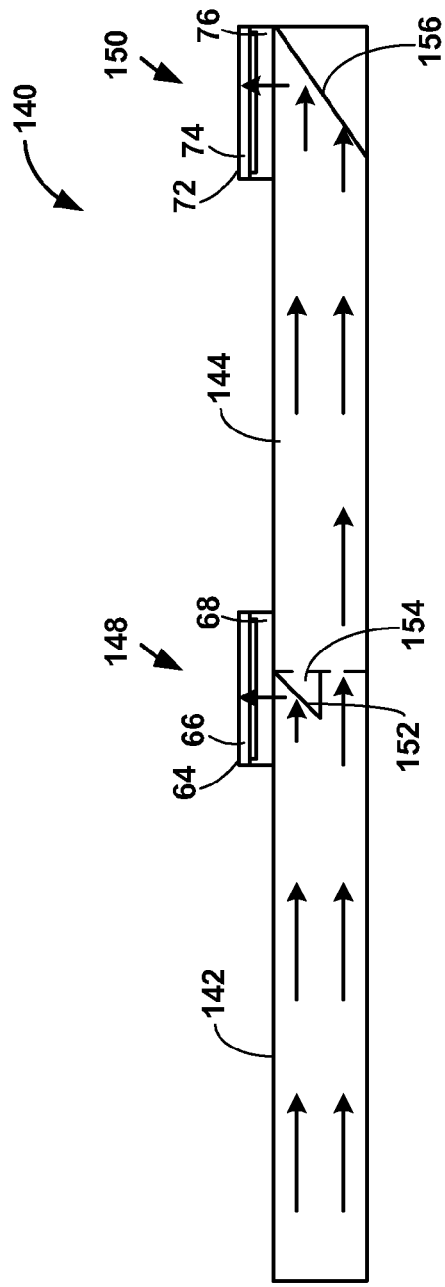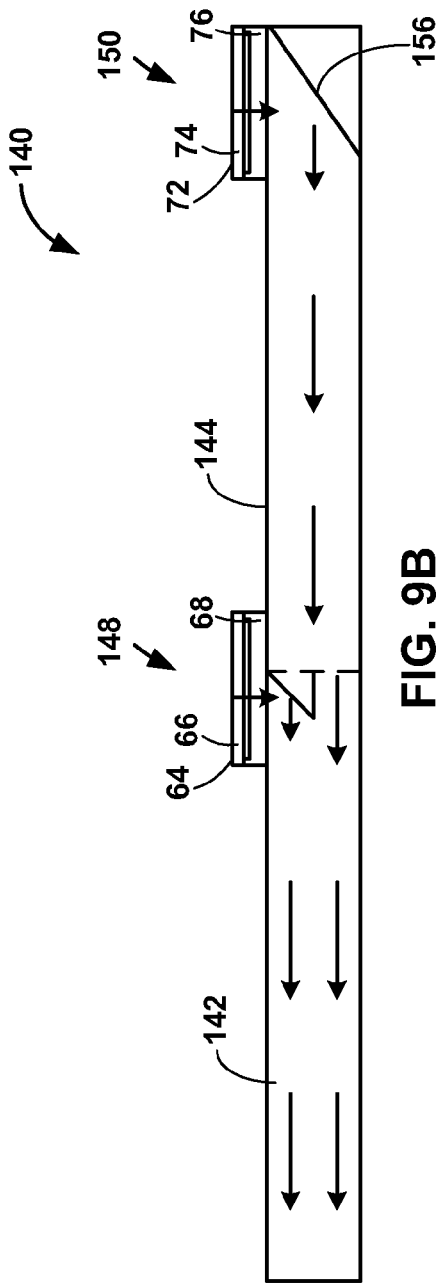

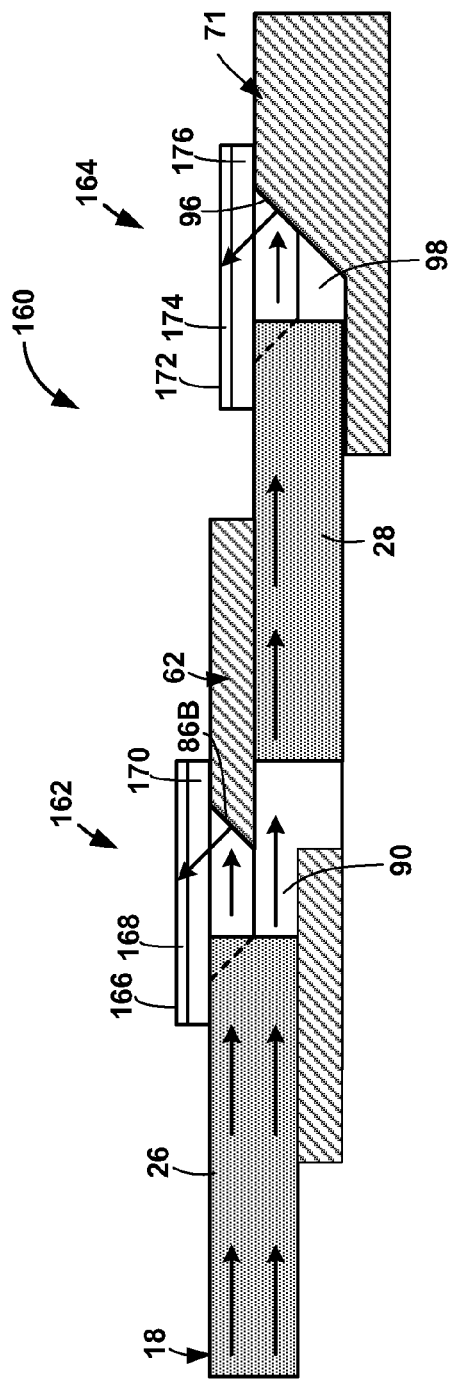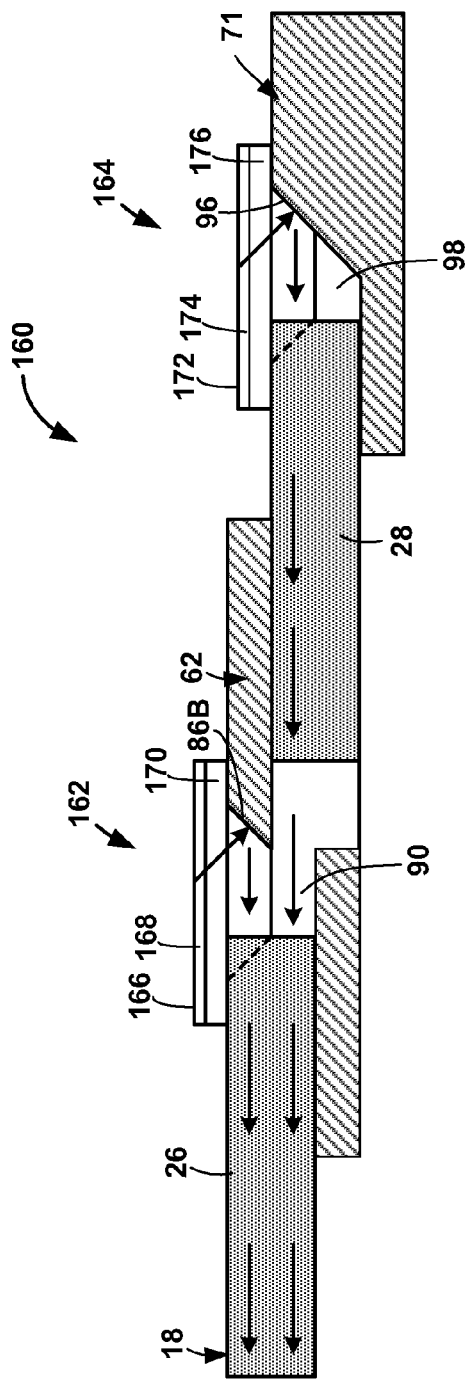
FIG. 10A
FIG. 10B

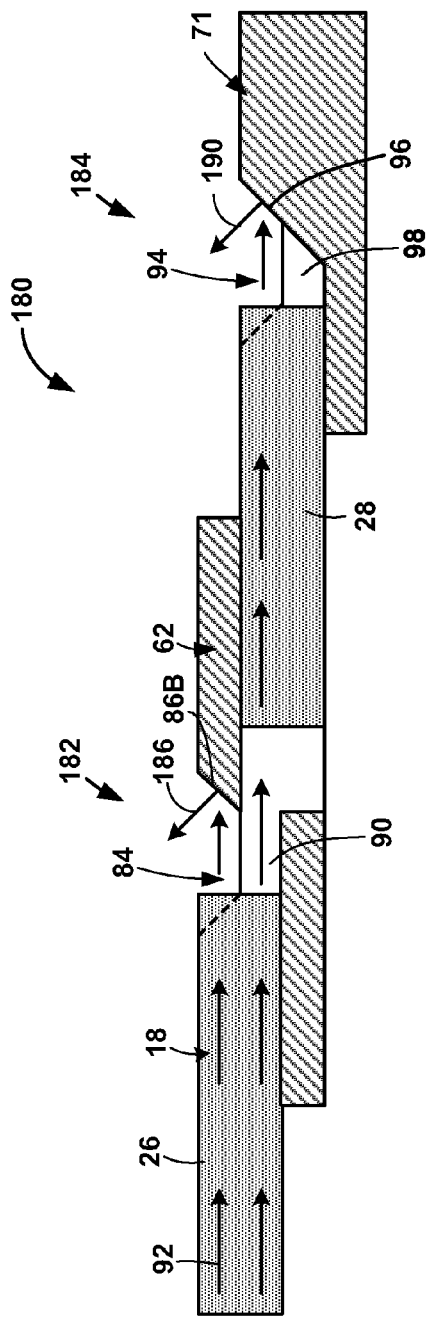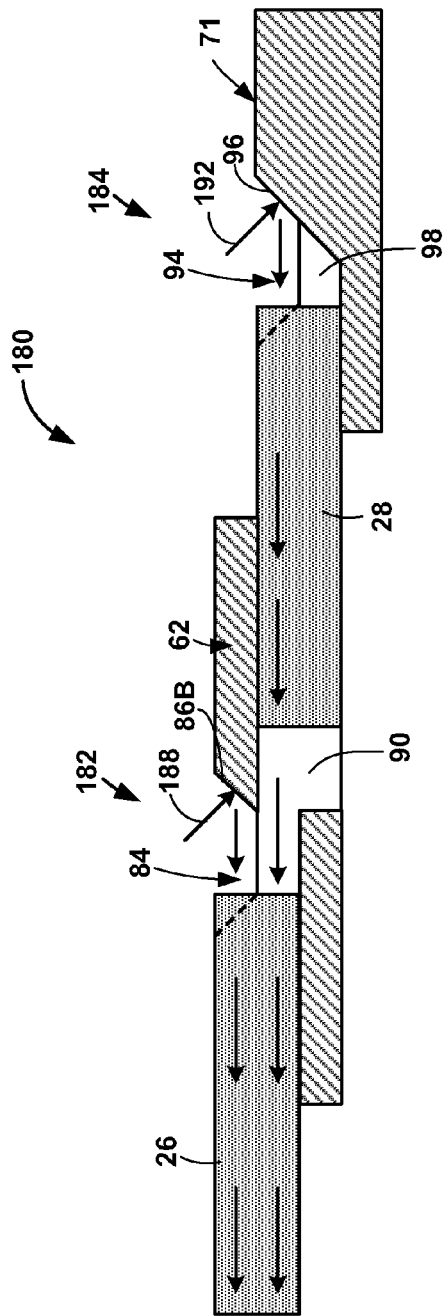

IMPLANTABLE MEDICAL SYSTEM INCLUDING MULTIPLE SENSING MODULES

TECHNICAL FIELD

The disclosure relates to medical devices and, more particularly, to medical devices that monitor one or more physiological parameters of a patient.

BACKGROUND

Some medical devices may monitor one or more physiological parameters of a patient on a temporary basis or on a chronic basis. Example sensors include pressure sensors that sense blood pressure or other pressure within the patient, accelerometers that sense muscle movement or patient posture, pulse oximeters or other reflectometers that sense a blood oxygen saturation level of the patient, acoustic sensors that sense cardiac activity, and the like. Some implantable sensors may be optical sensors that include a light source that emits light and a detector that senses the light. The intensity, velocity, phase or wavelength of the emitted light may be modulated in response to changes in a physiological parameter of the patient. The medical device may receive the modulated optical signal and determine a physiological parameter value of the patient based on one or more characteristics of the received optical signal.

For example, a pressure sensor may include a deflectable member that deflects in response to changes in pressure. As the deflectable member deflects in response to changes in pressure, the position or optical properties of the deflectable member may change, which may modulate light that is emitted by a light source of a medical system and traverses through the deflectable member or reflects off of the deflectable member. In this way, one or more characteristics of an optical signal that is generated when the emitted light traverses through the deflectable member may indicate a pressure characteristic of the patient.

SUMMARY

In general, the disclosure is directed toward a medical system that includes at least two optical sensing modules that each generate an optical signal that changes as a function of a common physiological parameter or different physiological parameters of a patient. The optical sensing modules may be coupled to a common light source via an optically transmissive member, which may be, for example, an optical fiber. In some examples, the sensing modules are distributed along a length of the optically transmissive member. The optical signals from a plurality of optical sensing modules may be multiplexed into an optical signal that transmits through the optically transmissive member. For example, the optical signals may be wavelength division multiplexed, whereby the optical signals generated by at least two of the sensing modules may have different wavelengths.

In some examples, at least a first optical sensing module that is closest to the light source along the length of the optically transmissive member may include a light dividing member to divide the light emitted by the light source. A first portion of the light may be directed toward the first optical sensing module and a second portion of the light may be directed toward a second optical sensing module that is placed downstream of the first sensing module in a direction substantially along the direction of light flow through the optically transmissive member and away from the light source. In other examples, the second sensing module may also include a light dividing member to further divide the second portion of the light, e.g., if one or more additional optical sensing modules are located along the optically transmissive member downstream of the second sensing module. The light dividing member may include, for example, a waveguide comprising a reflective surface or an optical beam splitter.

In some examples, the optical sensing modules may each include at least one reflective surface that directs at least a portion of the light emitted by the light source towards a sensing element of the sensing module or tissue of the patient. The sensing element or tissue may modulate the emitted light in response to changes in a physiological parameter of the patient, such as pressure, blood oxygen saturation level, patient movement, temperature, and the like. For example, changes in the amplitude, phase, frequency or velocity of the emitted light may be modulated in proportion to changes in the physiological parameter of the patient. The modulated light may propagate through the optically transmissive member to a receiver of the medical system that determines an absolute or relative physiological parameter value of the patient based on the modulated light. In this way, the modulated light may be an optical signal that indicates one or more physiological parameters of a patient.

In one aspect, the disclosure is directed to an implantable medical system comprising a light source that emits light, an implantable optically transmissive member optically coupled to the light source, a light dividing member that divides the light from the light source into at least a first portion and a second portion, a first sensing module optically coupled to the optically transmissive member, where the first sensing module receives the first portion of light and generates a first optical signal, and a second sensing module optically coupled to the optically transmissive member, where the second sensing module generates a second optical signal. The optically transmissive member guides the second portion of the light toward the second sensing module In another aspect, the disclosure is directed to an implantable medical system comprising a light source that emits light, a receiver, an optically transmissive member optically coupled to the light source and comprising a first segment and a second segment, a first sensing module optically coupled to the first and second segments of the optically transmissive member, wherein the light emitted by the light source propagates through the first segment to the first sensing module, and wherein the first sensing module generates a first optical signal based on the light emitted by the light source, and a second sensing module optically coupled to the second segment of the optically transmissive member, wherein light emitted by the light source propagates through the first and second segments to the second sensing module, and wherein the second sensing module generates a second optical signal based on the light emitted by the light source. The receiver receives the first and second optical signals via the optically transmissive member.

In another aspect, the disclosure is directed to an implantable medical system comprising means for emitting light from a light source within a medical device housing, wherein the light propagates through an optically transmissive member to first and second sensing modules optically coupled to the optically transmissive member, means for dividing the light into at least a first portion and a second portion, where the first sensing module receives the first portion of the light and the optically transmissive member guides the second portion of the light toward the second sensing module, means for receiving a first optical signal from the first sensing module, means for receiving a second optical signal from the second sensing module, and means for determining a physiological parameter value of a patient based on at least one of the first or second optical signals.

In another aspect, the disclosure is directed to an implantable medical system comprising means for controlling a light source within a medical device housing to emit light, wherein the light propagates through an optically transmissive member to first and second sensing modules optically coupled to the optically transmissive member, and the first sensing module comprising a light dividing member that divides the light into at least a first portion and a second portion, wherein the first sensing module receives the first portion of the light and the optically transmissive member guides the second portion of the light toward the second sensing module. The system further comprises means for receiving a first optical signal generated by the first sensing module based on the first portion of the light, means for receiving a second optical signal generated by the second sensing module based on the second portion of the light, and means for determining a physiological parameter value of a patient based on at least one of the first or second optical signals.

In another aspect, the disclosure is directed to a method comprising emitting light from a light source within a medical device housing, wherein the light propagates through an optically transmissive member to first and second sensing modules optically coupled to the optically transmissive member, dividing the light into at least a first portion and a second portion, where the first sensing module receives the first portion of the light and the optically transmissive member guides the second portion of the light toward the second sensing module, receiving a first optical signal from the first sensing module, receiving a second optical signal from the second sensing module, and determining a physiological parameter value of a patient based on at least one of the first or second optical signals.

In another aspect, the disclosure is directed to a method comprising controlling a light source within a medical device housing to emit light, wherein the light propagates through an optically transmissive member to first and second sensing modules optically coupled to the optically transmissive member, and the first sensing module comprising a light dividing member that divides the light into at least a first portion and a second portion, wherein the first sensing module receives the first portion of the light and the optically transmissive member guides the second portion of the light toward the second sensing module. The method further comprises receiving a first optical signal generated by the first sensing module based on the first portion of the light, receiving a second optical signal generated by the second sensing module based on the second portion of the light, and determining a physiological parameter value of a patient based on at least one of the first or second optical signals.

In another aspect, the disclosure is directed to a system comprising means for emitting light, an implantable means for transmitting light that is optically coupled to the means for emitting light, means for dividing the light from the light source into at least a first portion and a second portion, first means for sensing that is optically coupled to the means for transmitting light, wherein the first means for sensing receives the first portion of light and generates a first optical signal, and a second means for sensing that is optically coupled to the means for transmitting light, where the second means for sensing generates a second optical signal, and wherein the means for transmitting light guides the second portion of the light toward the second means for sensing.

In another aspect, the disclosure is directed to a computer-readable medium comprising instructions. For example, the computer-readable medium may store instructions. The instructions cause a programmable processor to perform any one or more of the techniques described herein.

The details of one or more examples of the disclosure are set forth in the accompanying drawings and the description below. Other features, objects, and advantages will be apparent from the description and drawings, and from the claims.

BRIEF DESCRIPTION OF DRAWINGS

FIGS. 6A and 6B are conceptual illustrations of light propagating through two optical sensing modules positioned along a common optically transmissive member.

FIGS. 8A and 8B are conceptual cross-sectional illustrations of an optically transmissive member and example sensing modules, where one of the sensing modules includes a beam splitter.

FIGS. 9A and 9B are conceptual cross-sectional illustrations of an optically transmissive member and example sensing modules, where the optically transmissive member comprises optical fibers including light deflection members.

FIGS. 10A and 10B are conceptual cross-sectional illustrations of an optically transmissive member and example sensing modules that each modify a frequency of light traversing through the respective sensing module.

FIGS. 11A and 11B are conceptual cross-sectional illustrations of an optically transmissive member and example sensing modules that sense a blood oxygen saturation level of a patient.

DETAILED DESCRIPTION

Figure 1:
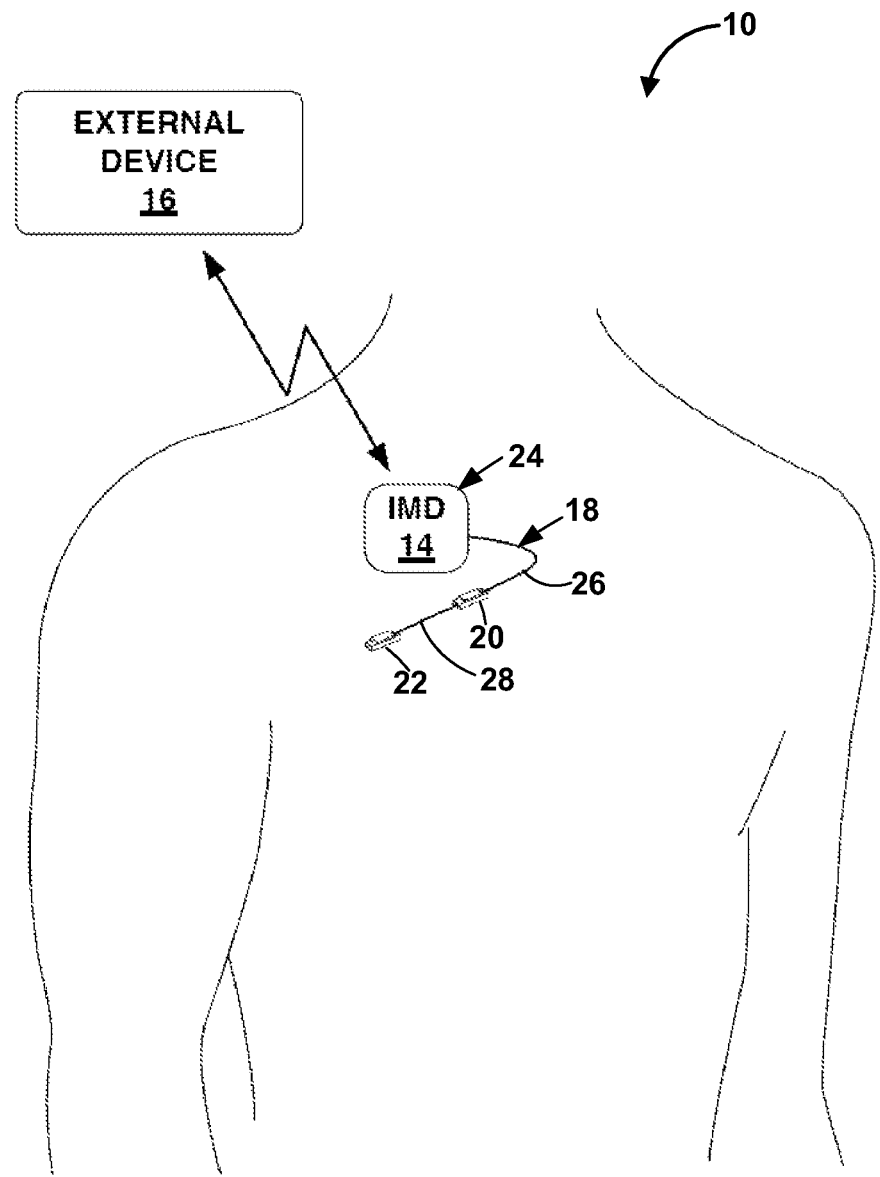
FIG. 1 is a conceptual diagram illustrating an example system that includes an implantable medical device (IMD) including a plurality of optical sensing modules.

FIG. 1 is a conceptual diagram illustrating an example system 10 that may be used to monitor one or more physiological parameters of patient 12, such as cardiac activity, temperature or an oxygen saturation level of blood of patient 12. Patient 12 ordinarily, but not necessarily, will be a human. Monitoring system 10 includes implantable medical device (IMD) 14 and external device 16. IMD 14 may be, for example, an implantable monitor that does not provide therapy (e.g., stimulation therapy) to patient 12. In other examples, IMD 14 may be configured to deliver stimulation to the heart of patient 12 or to deliver another type of therapy to patient 12 (e.g., delivery of a therapeutic agent). In such examples, IMD 14 may include one or more stimulation electrodes that may be positioned on housing 24 of IMD 14 and/or extend from leads that are coupled to housing 24. Neither IMD 14, external device 16 nor any of the figures are drawn to any particular scale.

In the example shown in FIG. 1, IMD 14 is implanted within a subcutaneous tissue layer of patient 12. In other examples, IMD 14 may be implanted within other tissue sites, such as a submuscular location. IMD 14 may be a temporary diagnostic tool employed to monitor one or more physiological parameters of patient 12 for a relatively short period of time (e.g., days or weeks), or may be used on a more permanent basis, such as to control therapy delivery to patient 12 or to monitor one or more physiological parameters of patient 12 on a chronic basis. In some examples of the latter use of IMD 14, a separate therapy delivery device, such as a fluid delivery device, pacemaker, cardioverter or defibrillator, may be implanted within patient 12. The therapy delivery device may communicate with IMD 14 via a wired connection or via wireless communication techniques. In other examples, as previously described, IMD 14 may be incorporated in a common housing with a therapy delivery device.

IMD 14 includes optically transmissive member 18, which is optically coupled to first optical sensing module 20 and second optical sensing module 22. As described in further detail below, optically transmissive member 18 optically couples sensing modules 20, 22 to a common light source and a common light receiver (e.g., a photodetector, such as a photodiode) that are disposed within housing 24 of IMD 14. Thus, optically transmissive member 18 may be useful for providing a common egress point for providing sensing modules 20, 22 with light and a common ingress point for receiving optical signals from sensing modules 20, 22. Optically transmissive member 18 may comprise any suitable optically conductive and transmissive material. In some examples, optically transmissive member 18 may comprise one or more optical fibers or one or more optical waveguides. Optically transmissive member 18, along with sensing modules 20, 22 and a receiver and optical emitter within housing 24 of IMD 14 may define an optical sensor that senses a physiological parameter of patient 12. Interfaces between optically transmissive member 18 and sensing modules 20, 22 may be hermetically sealed, e.g., with an epoxy.

Sensing modules 20, 22 may each generate an optical signal that changes as a function of a physiological parameter value of patient 12. Sensing modules 20, 22 are typically passive sensing modules that do not include electrical components. However, as described in further detail below, in some examples, sensing modules 20, 22 may include mechanical components, such as a sensing element. Sensing modules 20, 22 either reflect light emitted by an optical emitter within housing 24 of IMD 14 back to optically transmissive member 18 or collect emitted light that is reflected by another medium, such as tissue of patient 12. Thus, together with an optical emitter and optical detector (or more than one optical emitter or detector) within housing 24 of IMD 14, sensing modules 20, 22 may define optical sensors for sensing a physiological parameter of a patient.

In some examples, at least one of the sensing modules 20, 22 may comprise a sensing element that changes position or optical properties in response to a physiological parameter of patient 12. As an example, at least one of the sensing modules 20, 22 may comprise a deflectable member that is sensitive to pressure and deflects in response to pressure (e.g., fluid pressure), acoustic vibrations (e.g., resulting in acoustic pressure), temperature, or acceleration. In the case of an accelerometer, the deflectable membrane may comprise a proof mass flexural mount.

The light emitted by a light source of IMD 14 may interact with the sensing element, e.g., by transmitting through the sensing element or reflecting off of the sensing element. The sensing element may modulate a property of light that interacts with the sensing element. As the sensing element changes position or optical properties in response to changes in a physiological parameter of patient 12, a property of the light, such as the amplitude, phase, frequency or velocity, may change in proportion to the amount of position change or in response to the change in optical properties. Thus, the light may be modulated as a function of changes in a physiological parameter of patient 12. In this way, the optical signal that is generated by the respective sensing module 20, 22 and transmitted back to an optical detector within housing 24 of IMD 14 may be modulated in a manner indicative of relevant physiological parameter, e.g., pressure, vibrations, temperature, acceleration, and the like. Accordingly, in some cases, at least one of the sensing modules 20, 22 may comprise, for example, an optomechanical sensing module that generates an optical signal with the aid of mechanical elements.

A sensing module 20, 22 that is configured to modulate a property of emitted light in response to changes in pressure may facilitate monitoring of, for example, blood flow through tissue of patient 12. In addition, sensing acceleration (e.g., patient motion or movement of a specific muscle), temperature or an acoustic wave or signal may be indicative of cardiac activity of patient 12. In other examples, sensing modules 20, 22 may generate an optical signal indicative of a blood oxygen saturation level, cardiac activity (e.g., arterial pulses) or tissue perfusion of patient 12. In other examples of system 10, optically transmissive member 18 may be optically coupled to more than two sensing modules, such as three or more sensing modules. At least some of the sensing modules optically coupled to optically transmissive member 18 may be configured to sense different physiological parameters of patient 12 or the same physiological parameters of patient 12.

In the example shown in FIG. 1, optically transmissive member 18 is coupled to housing 24 of IMD 14. Housing 24 may comprise a biocompatible material that encloses various sensing and control circuitry for sensing, storing and/or transmitting one or more physiological parameters of patient 12 to another device, and, in some cases, a therapy delivery module for delivering therapy to patient 12 (e.g., electrical stimulation or a therapeutic agent). In addition, housing 24 may be hermetically sealed. Optical sensors 20, 22 may be discrete point sensors that may be interrogated substantially simultaneously to determine one or more physiological parameter values of patient 12. The physiological parameter value may be an absolute value or a relative value (e.g., that indicates a change in the physiological parameter).

In some examples, a processor within housing 24 may receive the optical signals generated by each of the sensing modules 20, 22 as a multiplexed optical signal and extract the optical signals from sensing modules 20, 22 based on known signal characteristics of the signal generated by sensing modules 20, 22. Examples of signal characteristics that may be used to extract signals generated by sensing modules 20, 22 from a single received through a common optically transmissive member 18 include, for example, the wavelength or phase of the optical signals, the time offset (e.g., due to an increased path length between sensing modules 20, 22) between the optical signals generated by sensors 20, 22, or the frequency domain components of the optical signals (e.g., using optical frequency domain reflectometry).

As described in further detail below, in some examples, wavelength division multiplexing may be implemented in order to multiplex multiple optical signals on a single optically transmissive member 18. Sensing modules 20, 22 may comprise optical components that receive light from a light source (or optical emitter) of IMD 14 or receive emitted light that is released into tissue and reflected back to the sensing module, and filter out a particular wavelength of light from the received light. In some examples, sensing modules 20, 22 may generate optical signals having different wavelengths.

Optically transmissive member 18 is optically coupled to at least one light source within housing 24. Optically transmissive member 18 may guide the light from the light source to sensing modules 20, 22 via a common egress point, which may help maximize the reliability of system 10, as well as minimize the size of system 10. It may be desirable to minimize the size of the components of system 10 in order to minimize the invasiveness of system 10. Optically transmissive member 18 couples a plurality of sensing modules 20, 22 to a processor or other components of IMD 14 enclosed within housing 24. Thus, system 10 including a common optically transmissive member coupling sensing modules 20, 22 to IMD 14 may be less invasive than a system in which a plurality of sensing modules are coupled to respective optically transmissive members that extend from housing 24.

Sensing modules 20, 22 that are distributed along a length of optically transmissive member 18 may facilitate monitoring one or more physiological parameters of patient 12 at more than one tissue site of patient 12. In particular, spatially distributed sensing modules 20, 22 enable system 10 to acquire physiological parameter data of patient 12 at more than one location with a common optically transmissive member 18, which minimizes the invasiveness of system 10. In some examples in which sensing modules 20, 22 monitor different physiological parameters of patient 12, the spatially distributed sensing modules 20, 22 may help position the sensing modules 20, 22 proximate respective target tissue sites. For example, if sensing module 20 monitors a blood oxygen saturation level of patient 12 and sensing module 20 monitors muscle movement of patient 12, system 10 may facilitate placement of sensing module 20 proximate a blood mass of patient (e.g., a blood vessel) and placement of sensing module 22 proximate to or within a muscle or other tissue of patient 12.

In some examples in which sensing modules 20, 22 monitor the same physiological parameter of patient, IMD 14 may determine an average physiological parameter value based on the optical signals from both of the sensing modules 20, 22. In other examples in which sensing modules 20, 22 monitor the same physiological parameter of patient 12, IMD 14 may compare the physiological parameter value of patient 12 at the tissue site proximate sensing module 20 and the tissue site proximate sensing module 22. In some examples, a processor within IMD 14 may determine which sensing module 20, 22 is more sensitive to changes in the physiological parameter of patient 12 and determine the physiological parameter value of patient 12 based on the optical signal from the sensing module 20, 22 determined to be more sensitive to changes in the physiological parameter.

In some examples of determining which sensing module 20, 22 is more sensitive to changes in the physiological parameter of patient 12, a clinician, a processor within IMD 14 or another device may cause a patient condition that results in a change in the physiological parameter value, and determine which sensing module 20, 22, if any, generated an optical signal that best indicated the physiological parameter value change. For example, if sensing modules 20, 22 generate optical signals that indicate a blood oxygen saturation level of patient 12, a clinician may induce a ventricular fibrillation in a heart of patient 12 and determine which sensing module 20, 22 indicated the greatest decrease in blood oxygen saturation level, which may result from the ventricular fibrillation. The clinician or processor of IMD 14 may then select the sensing module 20, 22 that sensed the greatest decrease in blood oxygen saturation level as the sensing module with which system 10 monitors the patient blood oxygen saturation level on a chronic basis.

In some examples, optically transmissive member 18 has a diameter of less than or equal to about 2 French (e.g., approximately 0.667 millimeters (mm)). However, other sizes are contemplated, and may depend on the implant site for patient 12, as well as the number of optical sensing modules that are coupled to member 18. As described in further detail below, optically transmissive member 18 may comprise optically transmissive segments 26, 28 that may be directly or indirectly optically coupled together in series. Light emitted by a light source within housing 24 of IMD 14 may propagate through segment 26 of optically transmissive member 18 prior to propagating through segment 28 of optically transmissive member 18.

As described in further detail below, system 10 may include one or more light dividing members that divide the light emitted by the light source of IMD 14, such that each optical sensing module 20, 22 receives a portion of the light. The light dividing members may permit a percentage of light emitted by the light source and propagating through light transmissive member 18 to be directed to each of the optical sensing modules 20, 22, where the percentage is less than about 100 percent (%). For example, in some examples, optical sensing modules 20, 22 may each receive about one half of the light emitted by the light source of IMD 14 and guided to the sensing modules 20, 22 via light transmissive member 18. In other examples, sensing module 20 may receive more light than sensing module 22 or sensing module 22 may receive more light than sensing module 20.

In some examples in which system 10 comprises three optical sensing modules distributed along optically transmissive member 18, each sensing module may receive approximately one-third of the light that is emitted by light source of IMD 14. As another example, in some examples in which system 10 comprises three optical sensing modules distributed along optically transmissive member 18, a first optical sensing module (positioned closest to the light source) may receive approximately 50% of the light, while a second optical sensing module positioned downstream of the first sensing module (relative to a direction of light flow away from the light source) may receive approximately 25% of the light, and the third optical sensing module positioned downstream of the second sensing module may receive approximately 25% of the light. However, other light distribution percentages are contemplated and may depend on the number of optical sensing modules that are optically coupled to optically transmissive member 18.

As previously indicated, sensing modules 20, 22 may each generate an optical signal that indicates a physiological parameter value of patient 12, which may be an absolute measurement or a relative change in the physiological parameter value. The optical signal may be generated, for example, when the light emitted by the light source of IMD 14 and directed to a reflective surface of the respective sensing module 20, 22 is reflected back to housing 24 of IMD 14. The reflected light may propagate through optically transmissive member 18 to a receiver within housing 24. The light may be modulated by an optical sensing element (e.g., a deflectable membrane that deflects in response to pressure, temperature, acoustic vibrations or acceleration), as described below with respect to FIGS. 5A-6B.

In other examples, the optical signal generated by at least one of the optical sensing modules 20, 22 may be modulated by tissue of patient 12. For example, as described below with respect to FIGS. 10A and 10B, light emitted by the light source of IMD 14 may be divided into a first portion that is directed at patient tissue by optical sensing module 20 and a second portion that is directed at patient tissue by optical sensing module 22. The light may then be reflected by blood of patient 12 in the tissue proximate the sensing modules 20 and/or 22. Optical sensing modules 20 and/or 22 may receive the reflected light, and the intensity of reflected light may indicate a blood oxygen saturation level of patient 12.

In some examples, IMD 14 may also include electrodes that sense electrical activity of patient's heart. For example, IMD 14 may generate an electrogram (EGM) or electrocardiogram (ECG) based on signals from the electrodes.

As described in further detail below with reference to FIG. 2, IMD 14 may include a memory that stores electrical signals generated by sensing modules 20, 22. In addition or alternatively, IMD 14 may transmit electrical signals or information derived from the electrical signals (e.g., a heart rhythm of patient 12) generated by sensing modules 20, 22 to another implanted or external device, such as external device 16. In some examples, a clinician may retrieve stored information from IMD 14 after explanting IMD 14 from patient 12. In other examples, the clinician (or other user) may interrogate IMD 14 with external device 16 while IMD 14 remains implanted within patient 12 in order to retrieve stored information from IMD 14.

IMD 14 may be useful for monitoring physiological parameters, such as the heart rate and blood oxygen saturation level, of patient 12. The monitored physiological parameter values may provide useful information for diagnosing a patient condition or formulating a treatment plan for patient 12. For example, if patient 12 experiences syncope, e.g., periodic fainting, IMD 14 may be used to determine the physiological parameters that are associated with the syncope. A clinician may review the associated physiological parameters to determine a potential cause of the syncopic events. For example, a clinician may determine whether any patient events occurred based on the recorded signals from optical sensors 18, 20.

External device 16 may be a handheld computing device or a computer workstation. External device 16 may include a user interface that receives input from a user, such as a clinician. The user interface may include, for example, a keypad and a display, which may for example, be a cathode ray tube (CRT) display, a liquid crystal display (LCD) or LED display. The keypad may take the form of an alphanumeric keypad or a reduced set of keys associated with particular functions. External device 16 can additionally or alternatively include a peripheral pointing device, such as a mouse, via which a user may interact with the user interface. In some examples, a display of external device 16 may include a touch screen display, and a user may interact with external device 16 via the display.

A user, such as a physician, technician, or other clinician, may interact with external device 16 to communicate with IMD 14. For example, the user may interact with external device 16 to retrieve physiological or diagnostic information from IMD 14. A user may also interact with external device 16 to program IMD 14, e.g., select values for operational parameters of monitor 14.

For example, the user may use external device 16 to retrieve information from IMD 14 regarding the rhythm of the heart of patient 12 (e.g., determined based on the signals from one or more of sensing modules 20, 22), trends of the heart rhythm over time or arrhythmia episodes. As another example, the user may use external device 16 to retrieve information from IMD 14 regarding other sensed physiological parameters of patient 12, such as blood oxygen saturation levels of patient 12. As another example, the user may use external device 16 to retrieve information from IMD 14 regarding the performance or integrity of IMD 14.

IMD 14 and external device 16 may communicate via wireless communication using any techniques known in the art. Examples of communication techniques may include, for example, low frequency or radiofrequency (RF) telemetry, but other techniques are also contemplated. In some examples, external device 16 may include a programming head that may be placed proximate to the patient's body near the implant site of IMD 14 in order to improve the quality or security of communication between IMD 14 and external device 16.

Figure 2:
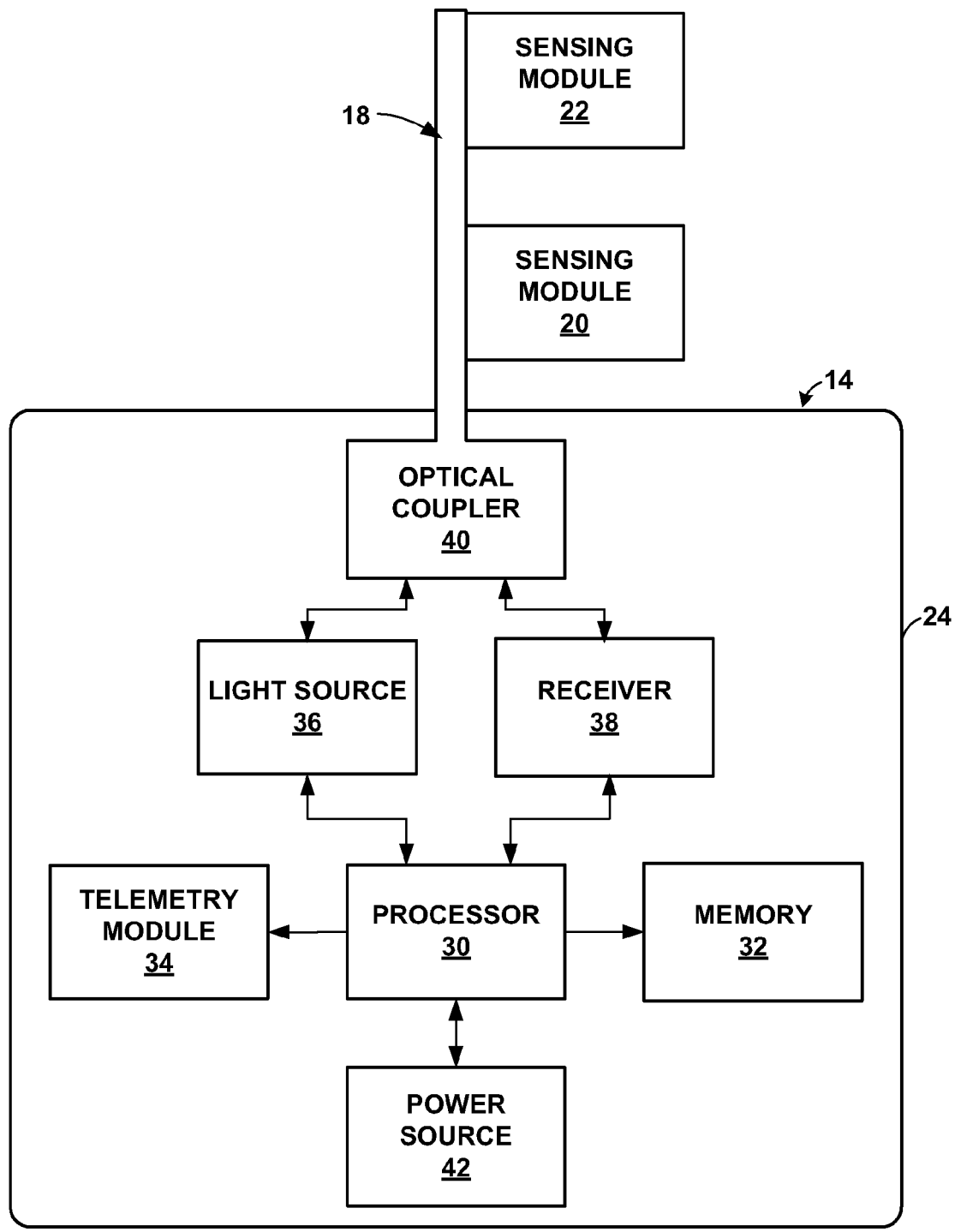
FIG. 2 is a functional block diagram of an example IMD that includes a plurality of optical sensing modules coupled to a common light source via an optically transmissive member.

FIG. 2 is a block diagram of an example IMD 14, optically transmissive member 18, and optical sensing modules 20, 22. In the example shown in FIG. 2, IMD 14 includes processor 30, memory 32, telemetry module 34, light source 36, receiver 38, optical coupler 40, and power source 42. Memory 32 includes computer-readable instructions that, when executed by processor 30, cause IMD 14 and processor 30 to perform various functions attributed to IMD 14 and processor 30 herein. Memory 32 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 30 may include any one or more microprocessors, controllers, digital signal processors (DSPs), application specific integrated circuits (ASICs), field-programmable gate arrays (FPGAs), or equivalent discrete or integrated logic circuitry, or combinations thereof. In some examples, processor 30 may include multiple components, such as any combination of one or more microprocessors, one or more controllers, one or more DSPs, one or more ASICs, or one or more FPGAs, as well as other discrete or integrated logic circuitry. The functions attributed to processor 30 herein may be embodied as software, firmware, hardware or any combination thereof.

Processor 30 controls light source 36 to emit light, which propagates through light transmission member 18 to sensing modules 20, 22. In some examples, light source 36 (also referred to as "optical emitter") may comprise one or more light emitting diodes (LEDs), laser diodes, vertical cavity surface emitting laser devices, and the like. For example, in examples in which sensing elements 20, 22 generate optical signals that indicate a blood oxygen saturation level of patient 12, light source 36 may comprise a red LED and an infrared (IR) LED. The red LED may emit light in the red portion of the visible light spectrum, such, but not limited to, light having a wavelength in a range of about 550 nanometers (nm) to about 750 nm. The IR LED may emit IR light in the IR portion of the light spectrum, such as, but not limited to, light having a wavelength in a range of about 750 nm to about 2.5 micrometers or greater. In some examples in which light source 36 includes more than one LED or other light emitter, processor 30 may control each LED to sequentially emit light, such that only one of the LEDs emits light at a time, e.g., one after the other in respective time slots.

Processor 30 also controls receiver 38 to receive optical signals generated by sensing modules 20, 22. The optical signals may include, for example, light emitted by light source 36 that is reflected by reflective surfaces of sensing modules 20, 22 or by blood in tissue of patient 12. In some examples, receiver 38 may comprise one or more photodetectors, such as photodiodes. In examples in which light source 36 emits a broad spectrum of light (e.g., light having a broad range of wavelengths), receiver 38 may include a photodiode that is sensitive to two or more wavelengths of light (e.g., light in the red spectrum and the IR spectrum) or receiver 38 may include multiple photodiodes that are each sensitive to a respective wavelength of light. Receiver 38 may be configured to convert received light into a current, voltage or digital count, which may be outputted as an electrical signal that is received by processor 30. In this way, processor 30 may receive optical signals generated by sensing modules 20, 22.

Optical signals received by receiver 38 may include information about one or more physiological parameters of patient 12. For example, an intensity (e.g., amplitude) of the optical signals received by receiver 38 from sensing modules 20, 22 may be indicative of hemodynamic function of patient 12, such as the oxygen saturation level of blood or the relative volume of blood in an artery of patient 12. As another example, an intensity, wavelength, phase, frequency or velocity of the optical signals received by receiver 38 from sensing modules 20, 22 may be indicative of pressure, temperature, acceleration or acoustic vibrations within patient 12. In examples in which receiver 38 comprises a photodiode, an electrical signal outputted by the detectors receiver 38 may be directly or inversely proportional to the amount of light (e.g., the intensity of light) incident on the photodiode, which may be the intensity of light guided to receiver 38 via optically transmissive member 18.

Sensing modules 20, 22 each modulate the light emitted by light source 36 based on a physiological parameter value of patient 12. In some examples, one or both of the sensing modules 20, 22 may be configured to receive light in a particular wavelength band as an indication of tissue perfusion or blood oxygen saturation levels. In addition, in some examples, one or both of sensing modules 20, 22 may be configured to receive light that is modulated by a deflection member in order to detect physiological parameters or conditions such as pressure, temperature, acoustic vibrations or acceleration. For example, as described in further detail below with respect to FIGS. 6A and 6B, in some examples, sensing modules 20, 22 may each include a deflectable member (e.g., a membrane) that changes position or optical properties in response to pressure that is applied to sensing modules 20, 22, in response to acoustical vibrations within patient 12, in response to temperature changes or in response to acceleration. As light propagates through the deflectable member, the amplitude of the light may be modulated, thereby generating an optical signal that indicates a pressure or acoustic activity within a particular tissue site of patient 12.

In other examples, sensing modules 20, 22 may be configured to monitor other physiological parameters of patient. For example, at least one of the sensing modules 20, 22 may be an optical reflectometer (e.g., a pulse oximeter), whereby the amplitude of light is modulated in response to the oxygen saturation level of tissue or a blood mass proximate to the respective sensing module 20, 22. In other examples, instead of or in addition to a deflectable member, sensing modules 20, 22 may comprise a deflectable beam that resonates in response to an electrical or optical excitation with resonance modulated by pressure, acoustic vibration or acceleration within patient 12. In such examples, the deflectable beam may change the frequency modulation of the optical signals generated by the sensing modules 20, 22 as a function of a physiological parameter of patient 12.

In some examples, sensing modules 20, 22 may each include an optical light filter that helps the sensing module 20, 22 generate an optical signal having a characteristic that is unique to the sensing module 20, 22. The signal characteristic may comprise, for example, different wavelengths, phases, frequencies or a time delay between the signals, which may be proportional the distance between sensing modules 20, 22 and housing 24 of IMD 14. While an optical signal having a particular wavelength is referred to herein, the optical signal may have more than one wavelength of light, e.g., a band of light that is narrower than the light emitted by light source 36. The different signal characteristics may help processor 30 distinguish between the optical signals generated by the sensing modules 20, 22, despite the common optically transmissive member 18 that guides the light from the sensing modules 20, 22 to a receiver within housing 24 of IMD 14. The light filter may comprise, for example, an optical material or multilayer dielectric that permits only a particular narrow band wavelength of light to transmit back to receiver 38. For example, the light filter may comprise a diffuse reflective surface or a material having a particular index of refraction.

In examples in which at least one of the sensing modules 20, 22 comprises a pressure sensor, e.g., as described below with respect to FIGS. 6A and 6B, the sensing module may include a reflective surface (e.g., a reflective coating on a deflectable member) that reflects light having a particular wavelength toward optically transmissive member 18, which may then guide the reflected light to receiver 38. The amplitude of the reflected light may change as the deflectable member of the respective sensing modules 20, 22 deflects in response to pressure exerted on the deflectable member. In examples in which at least one of the sensing modules 20, 22 comprises a optical reflectometer, receiver 38 may receive light emitted by light source 36 and reflected back to receiver 38 via blood-perfused tissue of patient 12 (e.g., tissue proximate to a blood mass, such as blood in an artery or other vasculature of patient). A filter may be positioned within the respective sensing module 20, 22 to permit only a light having a particular wavelength to transmit to receiver 38.

Receiver 38 may receive an optical signal comprising both the first and second optical signals generated by first and second sensing modules 20, 22, respectively. This optical signal comprising both the first and second optical signals may be referred to as an "aggregated" optical signal. Receiver 38 (or processor 30) may extract the first and second optical signals generated by sensing modules 20, 22 from the aggregated signal based on the characteristics by which the first and second optical signals differ. For example, receiver 38 may extract the first and second signals based on the known wavelengths or phase of the optical signals. Processor 30 may store the optical signals generated by sensing modules 20, 22, electrical signals generated by receiver 38, or values derived from the electrical signals generated by receiver 38 in memory 32.

Under the control of processor 30, optical coupler 40 may selectively couple light source 36 and receiver 38 to optically transmissive member 18, depending on whether light emission or light reception is desired. In some examples, optical coupler 40 may comprise a lens or an integrating sphere type assembly. In other examples, an optical fiber, waveguide or another optically transmissive member may couple light source and receiver 38 to optically transmissive member 18. For examples, two optical fibers may be fused together or otherwise coupled together to define a 2×1 optical coupler. Examples of suitable waveguides comprise waveguides formed of silicon or glass and comprises an optically transparent material such as lithium niobate. In other examples, light source 36 and receiver 38 may be positioned next to the input aperture of optically transmissive member 18.

Telemetry module 34 includes any suitable hardware, firmware, software or any combination thereof for communicating with another device, such as external device 16 (FIG. 1). Under the control of processor 30, telemetry module 34 may receive downlink telemetry from and send uplink telemetry to external device with the aid of an antenna, which may be internal and/or external. Processor 30 may provide the data to be uplinked to external device 16 and the control signals for the telemetry circuit within telemetry module 34, e.g., via an address/data bus. In some examples, telemetry module 34 may provide received data to processor 30 via a multiplexer.

The various components of IMD 14 are coupled to power source 42, which may include a rechargeable or non-rechargeable battery. A non-rechargeable battery may be selected to last for several years, while a rechargeable battery may be inductively charged from an external device, e.g., on a daily or weekly basis.

The block diagram shown in FIG. 2 is merely one example of an IMD 14. In other examples, IMD 14 may include a fewer number or a greater number of components. For example, in cases in which IMD 14 is incorporated with a medical device that delivers therapy to patient 12, IMD 14 may also include a therapy delivery module, such as an electrical stimulation generator or a fluid pump. In some examples, the therapy delivery module may deliver pacing, defibrillation or cardioversion pulses to a heart of patient 12, or may generate and deliver neurostimulation signals to a target tissue site within patient 12 (e.g., proximate to a spine or nerve, or to a target region of tissue that may or may not be near a nerve). The pulses or neurostimulation signals may be delivered to tissue of patient 12 with electrodes carried by leads that are coupled to housing 24 of IMD 14 or with electrodes on housing 24.

Although receiver 38 is shown to be separate from processor 30 in FIG. 2, in other examples, processor 30 may include the functionality attributed to receiver 38 described herein. In some examples, some of the components of IMD 14 shown in the example of FIG.2 may be located in another device. For example, although light source 36, receiver 38, and optical coupler 40 are shown in FIG. 2 to be incorporated within housing 24 (FIG. 1) of IMD 14 that also encloses other components, such as processor 30 and memory 32, in other examples, light source 36, receiver 38, and optical coupler 40 may be enclosed in a separate housing, such that light source 36, receiver 38, and optical coupler 40 may be separately implanted within patient 12. Light transmissive member 18 and sensing modules 20, 22 may be optically coupled to light source 36 that is enclosed in the housing separate from housing 24 of IMD 14.

In some examples, optical signals generated by at least one of the sensing modules 20, 22 and/or information based on the optical signals (e.g., physiological parameter values) may be uploaded from IMD 14 to a remote server, from which a clinician or another user may access the data to analyze the patient's condition. An example of a remote server is a server provided via the Medtronic CareLink® Network, available from Medtronic, Inc. of Minneapolis, Minn.

Figure 3:
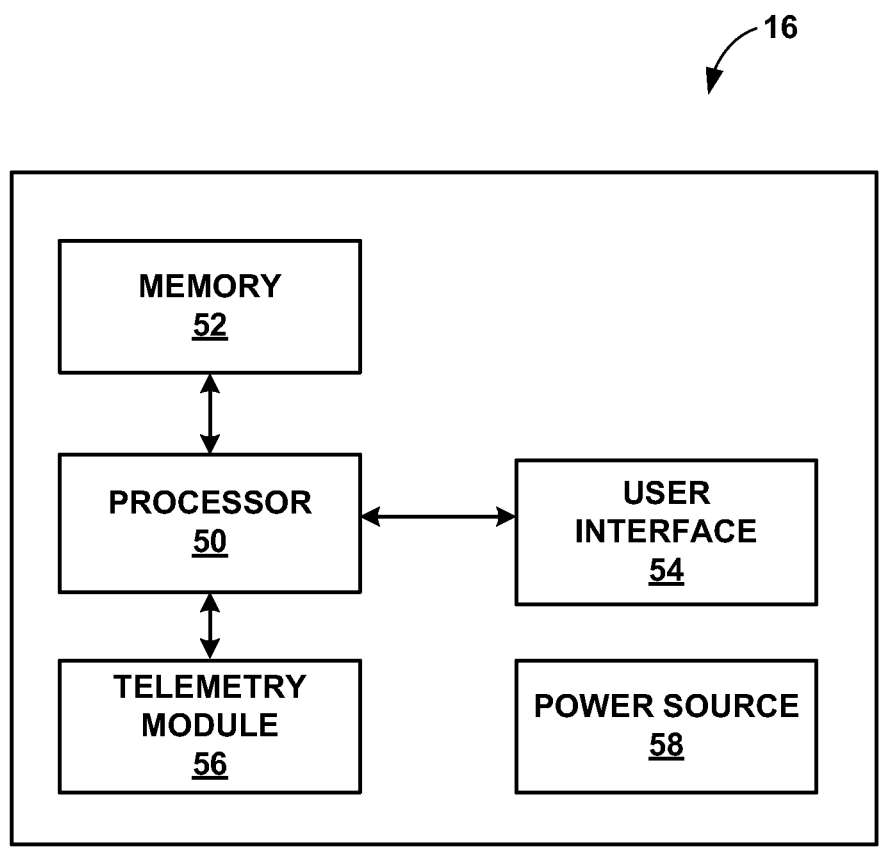
FIG. 3 is a functional block diagram of an example medical device programmer.

FIG. 3 is a block diagram of an example external device 16. As shown in FIG. 3, external device 16 includes processor 50, memory 52, user interface 54, telemetry module 56, and power source 58. External device 16 may be a dedicated hardware device with dedicated software for interrogating IMD 14 to obtain information stored in memory 32 (FIG. 2), and, in some examples, for programming IMD 14. Alternatively, external device 16 may be an off-the-shelf computing device running an application that enables external device 16 to communicate with IMD 14.

A user may use external device 16 to modify operating parameters of system 10. For example, the user may program the frequency at which light source 36 emits light and the frequency at which receives optical signals generated by optical sensing modules 20, 22. The clinician may interact with external device 16 via user interface 54, which may include display to present graphical user interface to a user, and a keypad or another mechanism for receiving input from a user.

Processor 50 may take the form one or more microprocessors, DSPs, ASICs, FPGAs, programmable logic circuitry, or the like, and the functions attributed to processor 50 herein may be embodied as hardware, firmware, software or any combination thereof. Memory 52 may store instructions that cause processor 50 to provide the functionality ascribed to external device 16 herein, and information used by processor 50 to provide the functionality ascribed to external device 16 herein. Memory 52 may include any fixed or removable magnetic, optical, or electrical media, such as RAM, ROM, CD-ROM, hard or floppy magnetic disks, EEPROM, flash memory, or the like. Memory 52 may also include a removable memory portion that may be used to provide memory updates or increases in memory capacities. A removable memory may also allow patient data to be easily transferred to another computing device, or to be removed before external device 16 is used to program therapy for another patient.

External device 16 may communicate wirelessly with IMD 14, e.g., using RF communication or proximal inductive interaction. This wireless communication is possible through the use of telemetry module 56, which may be coupled to an internal antenna or an external antenna. An external antenna that is coupled to external device 16 may correspond to the programming head that may be placed over the implant site of IMD 14. Telemetry module 56 may be similar to telemetry module 34 of IMD 14 (FIG. 2).

Telemetry module 56 may also be configured to communicate with another computing device via wireless communication techniques, or direct communication through a wired connection. Examples of local wireless communication techniques that may be employed to facilitate communication between external device 16 and another computing device include RF communication according to the 802.11 or Bluetooth specification sets, infrared communication, e.g., according to the IrDA standard, or other standard or proprietary telemetry protocols. In this manner, other external devices may be capable of communicating with external device 16 without needing to establish a secure wireless connection.

Power source 58 delivers operating power to the components of external device 16. Power source 58 may include a battery and a power generation circuit to produce the operating power. In some examples, the battery may be rechargeable to allow extended operation. Recharging may be accomplished by electrically coupling power source 58 to a cradle or plug that is connected to an alternating current (AC) outlet. In addition or alternatively, recharging may be accomplished through proximal inductive interaction between an external charger and an inductive charging coil within external device 16.

In other examples, traditional batteries (e.g., nickel cadmium or lithium ion batteries) may be used. In addition, external device 16 may be directly coupled to an alternating current outlet to power external device 16. Power source 58 may include circuitry to monitor power remaining within a battery. In this manner, user interface 54 may provide a current battery level indicator or low battery level indicator when the battery needs to be replaced or recharged. In some cases, power source 58 may be capable of estimating the remaining time of operation using the current battery.

Figure 4A:
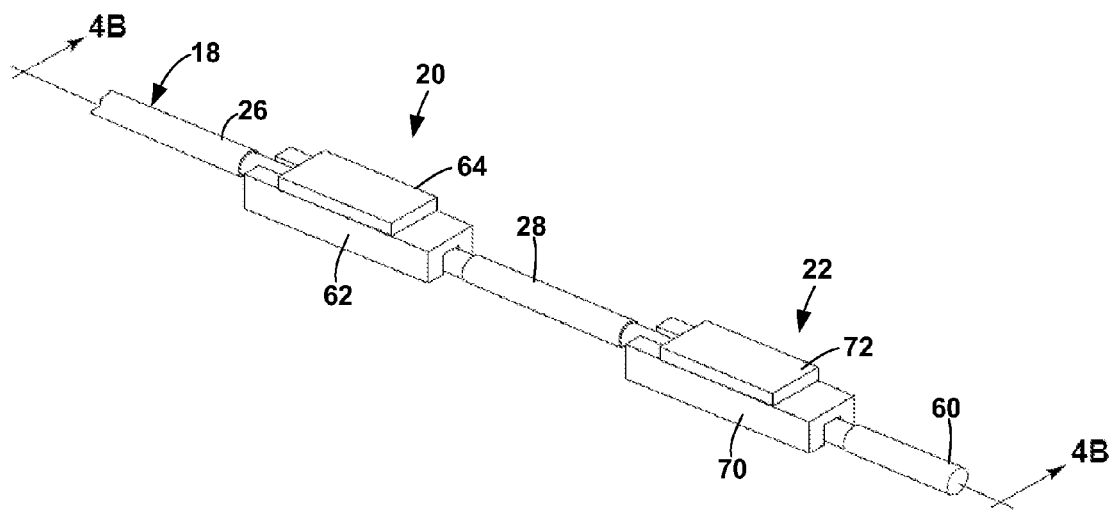
FIG. 4A is a perspective view of an example medical system including optical sensing modules that are coupled to a common optically transmissive member.
Figure 4B:
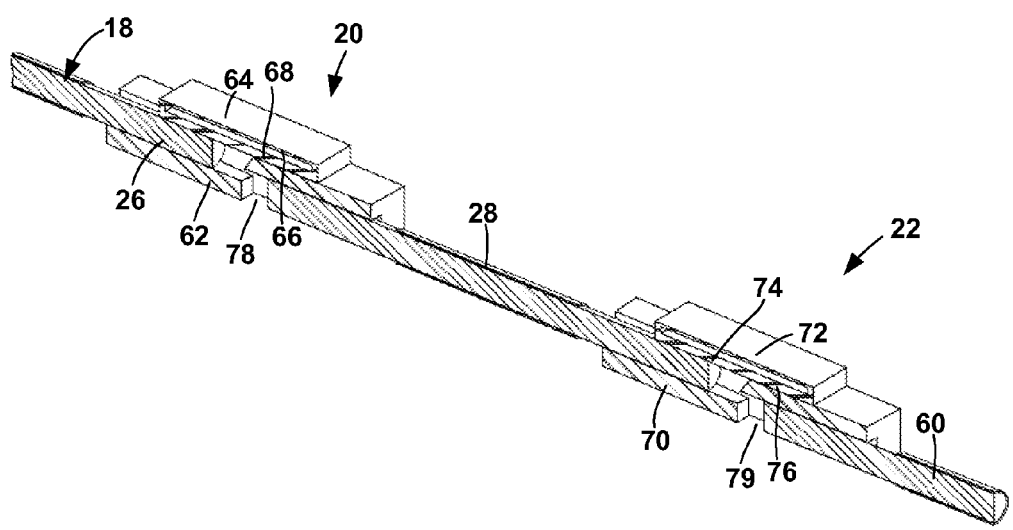
FIG. 4B is a cross-sectional view of the medical system of FIG. 4A taken along line 4B-4B in FIG. 4A.

FIG. 4A is a perspective view of optically transmissive member 18 and sensing modules 20, 22. FIG. 4B illustrates a cross-sectional view of optically transmissive member 18 and sensing modules 20, 22 taken along line 4B-4B in FIG. 4A. As previously indicated, optically transmissive member 18 may include a plurality of segments 26, 28, 60. In some examples, segments 28, 28, 60 may comprise optical fibers, a bundle of two or more optical fibers, or other types of waveguides. Segment 26 may extend between housing 24 of IMD 14 (FIG. 1) and first sensing module 20, segment 28 may extend between first sensing module 20 and second sensing module 22, and segment 60 may extend between second sensing module 22 and a distal end, or between second sensing module 22 and a third optical sensing module in examples in which system 10 includes at least three optical sensing modules. Segments 26, 28, 60 are optically conductive, such that light emitted by light source 36 (FIG. 2) may transmit from housing 24 of IMD 14 to each sensing module 20, 22 that is positioned along optically transmissive member 18.

In the example shown in FIGS. 4A and 4B, light emitted by light source 36 may propagate through segment 26 to first sensing module 20. As described in further detail below, first sensing module 20 comprises a light dividing member that divides the light from light source 36 into a first portion that is directed at first sensing module 20 and a second portion that is guided to second sensing module 22 via segment 28 of optically transmissive member 18.

In the example shown in FIGS. 4A and 4B, optical sensing modules 20, 22 include deflectable members that deflect in response to pressure, temperature, acoustic waves or acceleration. Thus, in the example shown in FIGS. 4A and 4B, optical sensing modules 20, 22 may be referred to as pressure sensors, temperature sensors, acoustic sensors or acceleration sensors. Optical sensing module 20 includes optical waveguide 62, reflective surface 64, deflectable member 66, and transparent member 68. As described in further detail below, optical waveguide 62 may define a structure that transmits light by internal reflection. In some examples, optical waveguide 62 defines an optical path that extends between segments 26, 28 of optically transmissive member 18. Light may traverse through the optical path by internal reflection. In some examples, waveguide 62 may comprise silicon. For example, waveguide 62 may be comprised of a dielectric material with a relatively high index of refraction that is surrounded by a material with a lower permittivity or air.

Waveguide 62 may be formed with the aid of microelectromechanical systems (MEMS) (or micromachines) processes by which a workpiece is machined to define waveguide 62. Accordingly, in some examples, waveguide 62 may be formed from a single piece of continuous material (e.g., a silicon wafer) or may be formed from multiple pieces that are mechanically coupled together, e.g., via welding, adhesive or another bonding technique. The MEMS machining technique may etch material to define various optical pathways and cavities of waveguide 62, which are described with respect to FIGS. 5A and 5B. In examples in which optical waveguide 62 is formed by a MEMS process, waveguide 62 may be referred to as a MEMS optical waveguide 62.

In one example, a MEMS batch process may be implemented in order to manufacture waveguide 62. For example, a silicon wafer (e.g., having a thickness of about 500 micrometers) may be wet etched (e.g., with potassium hydroxide (KOH)) to define an array of pockets. The array of pockets may be etched to a first depth in order to form a reflective surface of waveguide 62 (e.g., surface 86B described below with reference to FIGS. 5A and 5B). Wet etching a silicon wafer with KOH may result in a surface 86B that is oriented at about 54.7 degrees relative to a major surface of the silicon wafer. A refractory and reflective material may be applied to the angled side walls that result from the wet etching of the silicon wafer. Example refractory and reflective materials include, for example, gold or aluminum, although other materials are contemplated.

The silicon wafer may then be deep reactive ion etched to define a recess (e.g., recess 80 in FIGS. 5A and 5B) into which segment 26 of optically transmissive member 18 may be introduced and bonded. Similarly, the silicon wafer may be deep reactive ion etched to define a recess (e.g., recess 88 in FIGS. 5A and 5B) into which segment 28 of optically transmissive member 18 may be introduced and bonded. If multiple waveguides are formed from the same silicon wafer, a laser dice or other technique may be used to cut the waveguides from the wafer. The technique described herein is merely one example. Other techniques for forming waveguide 62 are contemplated.

Segment 26 of optically transmissive member 18 is optically coupled to a first end of waveguide 62 and segment 28 of optically transmissive member 18 is optically coupled to a second end of waveguide 62, where the first end is substantially opposite the second end. Segments 26, 28 are arranged such that light emitted by light source 36 (FIG. 2) may propagate through segment 26 prior to propagating through segment 28. In particular, as described in further detail with reference to FIGS. 5A-6B, light emitted by light source 36 (FIG. 2) may propagate through segment 26 of light transmissive member 18 and into waveguide 62. At least some of the light within waveguide 62 may be directed toward reflective surface 64 of optical sensing module 20, while at least some of the light within waveguide 62 may be directed toward segment 28 of light transmissive member 18. In this way, waveguide 62 may be a light divider that splits light from light source 36 into multiple components that are directed at different sensing modules 20, 22.

Waveguide 62 may include a surface that directs, e.g., by reflection or deflection, at least some light received from segment 26 of light transmissive member 18 toward reflective surface 64. Reflective surface 64 is configured to reflect at least some of the light back into waveguide 62 and toward housing 24 of IMD 14 (i.e., toward segment 26 of light transmissive member 18). Reflective surface 64 may be separate from deflectable member 66 or may be incorporated therewith. For example, reflective surface 64 may comprise a reflective material applied to an interior or exterior surface of deflectable member 66. Reflective surface 64 may comprise a diffusive reflective material that reflects light having a particular narrow band of wavelengths (such as a full width at half maximum (FWHM) dimension on the order of 10 nanometers or less). In this way, reflective surface 64 may act as a narrowband light filter that helps optical sensing module 20 generate an optical signal having a predetermined wavelength of light.

In other examples, reflective surface 64 may comprise a specular reflective material that reflects broadband light (e.g., light having a FWHM dimension on the order of 50 nanometers or greater) toward waveguide 62. Reflective surface 64 may reflect light toward optical waveguide 62. Thus, in the example shown in FIGS. 4A and 4B, the light that is transmitted to receiver 38 does not interact directly with tissue of patient 12. Rather, the light emitted by light source 36 is used to detect deflection and properties of the emitted light are changed proportional to the pressure on deflectable membrane 66. In other examples, the properties of the emitted light are changed proportional to the temperature, acoustic vibrations or patient movement to which deflectable membrane 66 is exposed.

Transparent member 68 may comprise glass or another material that permits light to transmit through transparent member 68 from waveguide 62 to deflectable member 66 and reflective surface 64. For example, transparent member 68 may be transparent at wavelengths of interest and refractory. Transparent member 68 may help hermetically seal waveguide 62, e.g., from moisture or other contaminants that waveguide 62 may be exposed to when implanted within patient 12. Deflectable membrane 66 and transparent member 68 may be joined together to form a hermetic seal. The hermetic seal may be formed, e.g., by coupling deflectable membrane 66 and transparent member 68 together with an epoxy, or deflectable membrane 66 and transparent member 68 may brazed together or welded together (e.g., laser welded).

Deflectable member 66 is configured to deflect as pressure is applied to an external surface of sensing module 20. As shown in FIGS. 4B, a pressure cavity (e.g., filled with air) may be located under membrane 66 in order to provide room for membrane 66 to deflect. Deflectable member 66 may comprise any suitable material, such as a refractory material (e.g., glass, silicon or titanium). As deflectable member 66 deflects, the optical properties of deflectable member 66 may change. Accordingly, light that propagates through deflectable member 66 and reflects off of reflective surface 64 may change characteristics, such as intensity (e.g., amplitude), wavelength, frequency or velocity, based on the deflection of deflectable member 66. In this way, deflectable member 66 may modulate the light that traverses through waveguide 62 based on the amount of pressure that is exerted on sensor 20. The light that reflects off of reflective surface 64 may be an optical signal that is transmitted to receiver 38 (FIG. 2) of IMD 14 via light transmissive member 18. Receiver 38 may determine one or more physiological parameter values of patient 12 based on the optical signal generated by optical sensing module 20.

As one example of how deflectable member 66 may modulate a property of light that transmits through member 66, when pressure is applied to deflectable membrane 66, deflectable membrane 66 may strain and deflect inward toward optical waveguide 62. When reflective membrane 66 is at an initial position, light coupling back into waveguide 62 may be at an initial level. As the membrane 66 deflects, the coupling efficiency of membrane 66 may change. As a result, the amplitude of the optical signal that is reflected back into waveguide 62 may decrease as membrane 66 deflects. Thus, membrane 66 may modulate the amplitude of an optical signal as a function of the amount of deflection exhibited by membrane 66. In other examples, sensing module 20 may include a grating or another means of optical filtering that shifts the wavelength, or phase/frequency of a pulsed signal that is directed at deflectable membrane 66. For example, in some cases, the pressure on deflectable membrane 66 may cause the diffraction pitch of membrane 66 to change, so that a peak of the wavelength of the light that is reflected by reflective surface 64 is shifted. As a result, the phase of light may be shifted as the light transmits through deflectable member 66. Thus, the phase of the light that is received by receiver 38 may indicate the particular pressure level within patient 12 or a change in pressure level.

Optical sensing module 22 includes waveguide 70, reflective surface 72, deflectable member 74, and transparent member 76, which are similar to waveguide 62, reflective surface 64, deflectable member 66, and transparent member 68, respectively, of optical sensing module 20. In some examples, substantially all of the light that transmits through optical sensing module 20 and through segment 28 of optically transmissive member 18 may be directed toward deflectable member 74 and reflective surface 72 by waveguide 70. In other examples, such as examples in which at least one additional optical sensing module is optically coupled to segment 60 of optically transmissive member 18, downstream of sensing module 22 relative to a direction of light flow away from light source 36 (FIG. 2), waveguide 70 may divide the light received from segment 28 of optically transmissive member 18. For example, waveguide 70 may direct a portion of the light traveling through waveguide 70 toward reflective surface 72 and deflectable member 74, and direct another portion of the light through waveguide 70 and to segment 60 of light transmissive member 18 without propagating through deflectable member 74.

Just as with optical sensing module 20, optical sensing module 22 generates an optical signal as light propagates through deflectable member 74 and reflects off of reflective surface 72. The optical signal generated by optical sensing module 22 may propagate through segments 26, 28 of light transmissive member 18 and through waveguide 62 to receiver 38 (FIG. 2) of IMD 14. Processor 30 of IMD 14 (FIG. 2) may determine one or more physiological parameter values of patient 12 based on the optical signal generated by optical sensing module 22.

As previously described, in order to help processor 30 of IMD 14 distinguish between the optical signals generated by sensing modules 20, 22, sensing modules 20, 22 may each generate an optical signal having a particular wavelength. For example, sensing modules 20, 22 may include optical components that return only selected bands of light, where one band corresponds to one sensor 20 and the other corresponds to the other sensor 22. Light source 36 (FIG. 2) may emit broadband light, which may be transmitted to sensing modules 20, 22 via optically transmissive member 18. Sensing modules 20, 22 may then reflect light having a wavelength within a narrow band (narrower than the broadband light emitted by light source 36) that is specific to the respective sensing module 20, 22. For example, reflective surfaces 64, 72 of sensing modules 20, 22, respectively, may each comprise a diffuse reflective coating or surface that acts as a narrowband filter by reflecting only a certain wavelength of light or a certain band of light back into the respective waveguides 62, 70. In some examples, reflective surfaces 64, 72 may comprise a diffuse reflective coating applied to the respective deflectable members 66, 74. In other examples, reflective surfaces 64, 72 may comprise a diffuse reflective member that is coupled to the respective deflectable members 66, 74, e.g., via an optically conductive adhesive or welding.

The optical signals generated by sensing modules 20, 22 may propagate through optically transmissive member 18 to receiver 38 at substantially the same time. Processor 30 may demodulate the optical signals based on the known wavelengths of the optical signals, which may be determined based on the wavelength of light that sensing modules 20, 22 generate. In some examples, the wavelength of the optical signal that sensing modules 20, 22 generate may be based on the wavelength of light that reflective surfaces 64, 72 are configured to reflect back into the respective waveguides 62, 70, which may be based on, for example, the index of refraction of reflective surfaces 64, 72. In this way, system 10 may implement wavelength division multiplexing to operate optical sensing modules 20, 22 that are coupled to a common light source 36 and determine one or more physiological parameter values of patient 12 based on optical signals generated by optical sensing modules 20, 22.

In the example shown in FIGS. 4A and 4B, optical waveguides 62, 70 define cavities 78, 79. In order to help hermetically seal sensing modules 20, 22, as well as any interfaces between optical waveguides 62, 70 and optically transmissive member 18, cavities 78, 79 may be hermetically sealed in some examples. For example, an epoxy may be introduced into cavities 78, 79 or an epoxy seal or cover plate may otherwise be formed over or within cavities 78, 79 to hermetically seal cavities 78, 79.

In other examples of the sensing system shown in FIGS. 4A and 4B, segment 28 of optically transmissive member 18 may interface with segment 26, e.g., through an opening within waveguide 62, and an epoxy may seal the interface between segments 26, 28. Similarly, in some examples, segment 28 of optically transmissive member 18 may interface with segment 60, e.g., through an opening within waveguide 70, and an epoxy may seal the interface between segments 60, 72.

Figure 5A:
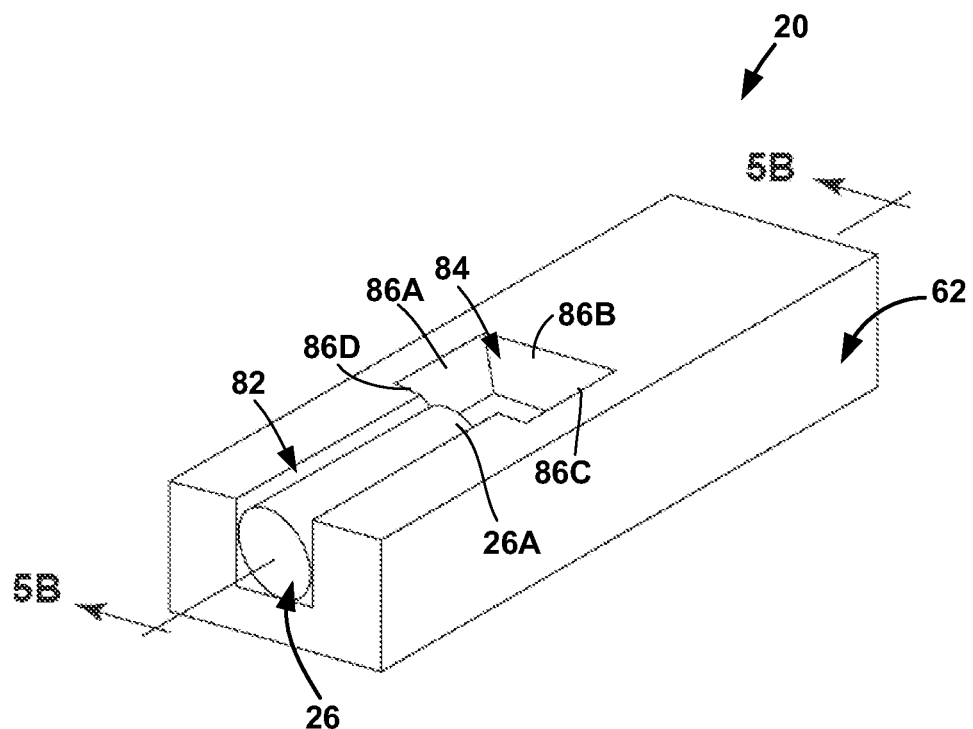
FIG. 5A is a perspective view of an example optical sensing module.
Figure 5B:
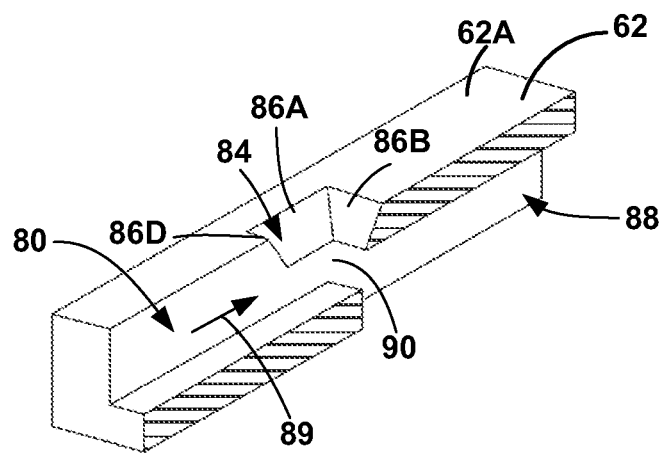
FIG. 5B is a cross-sectional view of the optical sensing module of FIG. 5A taken along line 5B-5B in FIG. 5A.

FIG. 5A is a perspective view of waveguide 62 of optical sensing module 20 and segment 26 of optically transmissive member 18. FIG. 5B is a cross-sectional view of waveguide 62 taken along line 5B-5B in FIG. 5A. Segment 26 is not shown in FIG. 5B. In addition, reflective surface 64, deflectable member 66, and transparent member 68 of sensing module 20 are not illustrated in FIGS. 5A and 5B. Waveguide 70 of sensing module 22 may be substantially similar to waveguide 62.

As FIGS. 5A and 5B illustrate, waveguide 62 defines a recess 80 that is configured to receive segment 26 of optically transmissive member 18. Recess 80 may be defined using any suitable technique, such as etching (e.g., reactive ion etching) of a silicon wafer. In some examples, in order to help hermetically seal sensing module 20, an epoxy or another material may be positioned within space 82 between an outer surface of segment 26 and waveguide 62. The epoxy or other material may also help secure segment 26 to waveguide 62. In other examples, other mechanisms for securing segment 26 within recess 80 defined by waveguide 62 may be employed. For example, an adhesive may be applied to at least part of the outer surface of segment 26 or at least a part of the inner surface of recess 80.

Waveguide 62 defines optical cavity 84, which includes surfaces 86A-86D in the example shown in FIGS. 5A and 5B. In examples in which waveguide 62 comprises silicon, surfaces 86A-86D are substantially nonorthogonal to top surface 62A of waveguide 62, and substantially nonparallel to each other. Top surface 62A may be substantially planar in some examples. When silicon is etched to define optical cavity 84, the etching process may result in the nonparallel surfaces 86A-86D of the optical cavity 84 because of the crystalline structure of silicon. In other examples, such as examples in which waveguide 62 comprises a material other than silicon, at least two of the surfaces 86A-86D may be substantially parallel to each other.

Segment 26 of optically transmissive member 18 may guide light from light source 36 (FIG. 2) to optical cavity 84 defined by waveguide 62. For example, segment 26 may be positioned within recess 80 such that light propagating through segment 26 enters optical cavity 84. For example, in examples in which segment 26 comprises an optical fiber, distal end 26A of segment 26 may be cleaved such that light may transmit from distal end 26A of segment 26 into cavity 84. A portion of the light that exits segment 26 and into optical cavity 84 may reflect off of surface 86B of optical cavity 84. The configuration of surface 86B relative to the path of light through optical cavity 84, which is indicated by arrow 89, may help direct light toward reflective surface 64 and deflectable member 66 (not shown in FIGS. 5A and 5B) of sensing module 20. That is, light incident on surface 86B may be directed toward reflective surface 64 and deflectable member 66. For example, surface 86B may comprise a specular reflective material, such as a material that defines a mirrored surface. In some examples, at least a portion of surface 86B may be coated with a reflective coating, such as gold or aluminum. Other reflective materials are contemplated. In other examples, surface 86B may comprise a diffuse reflective surface that only directs light having a particular wavelength toward reflective surface 64 and deflectable member 66. In such examples, reflective surface 64 may comprise a specular reflective material that reflects light having the same wavelength back into waveguide 62.

Another portion of the light that exits segment 26 and into optical cavity 84 may propagate through optical cavity 84 and into recess 88 defined by waveguide 62. As with recess 80, recess 88 may be defined using any suitable technique, such as reactive ion etching of a silicon wafer. As described in further detail with reference to FIGS. 6A and 6B, segment 28 of optically transmissive member 18 may be positioned within recess 88 to capture at least some of the light that transmits through segment 26 and optical cavity 84. The captured light may then propagate through segment 28 to optical sensing module 22 (FIGS. 4A and 4B).

102 Recess 80, optical cavity 84, and recess 88 define an optical pathway 90 through waveguide 62. Light introduced into waveguide 62 by optically transmissive member 18 may traverse through optical pathway 90. As shown in FIG. 5B, surface 86B of waveguide 62 extends partially into optical pathway 90, thereby partially occluding optical pathway 90. Surface 86B may direct a first portion of the light that is traversing through pathway 90 towards reflective surface 64 and deflectable member 66 (not shown in FIGS. 5A and 5B)

of sensing module 20, while the remaining light may continue propagating through pathway 90 and into segment 28 of optically transmissive member 18. In this way, surface 86B of optical cavity 84 splits light emitted by light source 36 of IMD 14 into at least two portions, whereby a first portion is directed toward reflective coating 64 and deflectable member 66 of sensing module 20 by surface 86B and a second portion is directed toward sensing module 22 (not shown in FIGS. 5A and 5B) via optical pathway 90. For example, the second portion of the light may be directed toward sensing module 22 via segment 28 of optically transmissive member 18 (FIGS. 4A and 4B).

In some examples, optical pathway 90 and surface 86B of waveguide 62 may configured such that surface 86B of optical cavity 84 occludes approximately half of optical pathway 90 to direct approximately 50% of the light propagating through pathway 90 into waveguide 62 toward reflective surface 64 and deflectable member 66 (not shown in FIGS. 5A and 5B) of sensing module 20 and to direct approximately 50% of the light toward sensing module 22 via optical path 90. The light directed toward reflective surface 64 and deflectable member 66 of sensing module 20 surface 86B of cavity 84 may be used to sense a physiological parameter value of patient 12.

In some examples, waveguide 70 of optical sensing module 22 may also include a reflective surface that at least partially occludes an optical path through waveguide 70 such that less than 100% (e.g., approximately 50%) of the light propagating through the waveguide 70 is directed toward reflective surface 72 and deflectable member 74 of sensing module 22. In some examples, the remaining percentage of light that propagates through waveguide 70 may then be directed toward additional sensing modules that may be optically coupled to optically transmissive member 18. In other examples, waveguide 70 of optical sensing module 22 may include a reflective surface that fully occludes an optical path through waveguide 70 such that approximately 100% of the light propagating through the waveguide 70 is directed toward reflective surface 72 and deflectable member 74 of sensing module 22.

Other light distribution percentages between sensing modules 20, 22 are contemplated. For example, in some examples, more light may be directed at optical sensing module 20 compared to optical sensing module 22, while in other examples, more light may be directed at optical sensing module 22 compared to optical sensing module 20.

106 FIGS. 6A and 6B are conceptual cross-sectional illustrations of segments 26, 28 of optically transmissive member 18 and sensing modules 20, 22. FIG. 6A illustrates the path of light from light source 36 of IMD 14 (FIG. 2) to optical sensing modules 20, 22, and FIG. 6B illustrates the path of optical signals from optical sensing modules 20, 22 toward receiver 38 of IMD 14 (FIG. 2). The path of light shown in FIG. 6A is substantially opposite the path of light shown in FIG. 6B.

In FIG. 6A, light propagates through segment 26 of optically transmissive member 18 in a direction indicated by arrows 91. As light traverses through waveguide 62, the light is split into at least two portions. A first portion of the light is directed toward reflective surface 64 and deflectable member 66 of sensing module 20, as indicated by arrow 92, and a second portion of the light traverses through optical path 90 defined by waveguide 62 and into segment 28 of optically transmissive member 18, as indicated by arrow 93. In particular, as shown in FIG. 6A, light 92 incident on surface 86B of optical cavity 84 is directed toward reflective surface 64 and deflectable member 66. Light 93 that is not incident on surface 86B of optical cavity 84 is substantially unobstructed and continues to propagate through optical pathway 90 of waveguide 62 and into segment 28 of optically transmissive member 18.

Segment 28 of optically transmissive member 18 is disposed within recess 88 of waveguide 62. As with segment 26, an epoxy or another material may be positioned within the space between an outer surface of segment 28 and waveguide 62 to help hermetically seal waveguide 62. In addition, in some examples, segment 28 may be secured to waveguide 62 with the aid of, for example, an adhesive or welding. In examples in which segment 28 comprises an optical fiber, a proximal end 28A may be cleaved such that light may transmit from optical pathway 90 into segment 28.

Segment 28 of optically transmissive member 18 guides light into waveguide 70 of sensing module 22. Waveguide 70 defines optical cavity 94, which is substantially similar to optical cavity 84 of optical sensing module 20. At least a portion of the light that is introduced into waveguide 70 by segment 28 may be directed toward reflective surface 72 and deflectable member 74 of optical sensing module 22, as indicated by arrow 97. In the example shown in FIG. 6A, surface 96 of optical cavity 94, which is similar to surface 86B of optical cavity 84 of sensing module 20, may be reflective. Accordingly, the angular orientation of surface 96 relative to the path of light through waveguide 70 may be selected such that light 97 directed at surface 96 is directed toward reflective surface 72 and deflectable member 74 of optical sensing module 22.

In examples in which one or more additional optical sensing modules are positioned downstream of optical sensing module 22 relative to a direction of light propagation away from light source 36 of IMD 14, at least a portion of the light introduced into waveguide 70 may propagate through waveguide 70 without being directed toward reflective surface 72 and deflectable member 74. Segment 60 (FIG. 5A) of optically transmissive member 18 may be positioned to receive at least some of the light that propagates through waveguide 70 and guide the light to another sensing module. In such examples, surface 96 of waveguide 70 may at least partially occlude optical pathway 98 through waveguide 70 to split at least a portion of the light propagating through waveguide 70 into at least a first portion that is directed toward reflective surface 72 and deflectable member 74 and a second portion that continues through optical pathway 98 to segment 60 (FIG. 5A) of optically transmissive member 18.

As previously indicated, sensing modules 20, 22 each generate an optical signal that indicates at least one physiological parameter value of patient 12. The sensing modules 20, 22 may be modify an intensity of light in response to a physiological phenomena of patient 12, such as pressure proximate to the respective sensing modules 20, 22, the blood oxygen saturation level, and the like. The type of sensing module 20, 22 selected for system 10 may be based on the physiological parameter of patient 12 that is monitored by system 10. In the example shown in FIGS. 6A and 6B, sensing modules 20, 22 are each configured to monitor a pressure or sounds (e.g., sounds associated with cardiac activity) within patient 12.

As previously indicated, light that is propagating through waveguide 62 in a first direction away from light source 36 of IMD 14 may be directed toward reflective surface 64 and deflectable member 66 by surface 86B. The light may then reflect off of surface 64 and back toward surface 86B of optical cavity 84 of waveguide 62. Surface 64 may be a diffuse reflecting surface that only reflects light having a predetermined wavelength back toward surface 86B of optical cavity 84. As the light travels through deflectable member 66, the amplitude or another characteristic of the light may be modified. As deflectable member 66 deflects in response to pressure applied to optical sensing module 20, the amplitude of the light may be modulated, thereby generated an optical signal that indicates a pressure within patient 12.

In other examples, the light emitted by light source 36 may be directed onto and reflect off of a surface of deflectable member 66. In this manner, deflectable member 66 is both the light modulator and the reflector, e.g., includes the reflective surface 64.

As shown in FIG. 6B, the index of refraction of reflective surface 64 may be selected such that light that reflects off of surface 64 is directed toward surface 86B of optical cavity 84. Light incident on surface 86B, as indicated by arrow 100 in FIG. 6B, is directed toward segment 26 of optically transmissive member 18, which may then direct the light, i.e., the optical signal generated by sensing module 20, toward receiver 38 of IMD 14 (FIG. 2).

Light that is propagating through waveguide 70 of optical sensing module 22 in a first direction away from light source 36 of IMD 14 may be directed toward reflective surface 72 and deflectable member 74 by surface 96 of optical cavity 94. The index of refraction of reflective surface 72 may be selected such that light incident on surface 72 is directed back toward surface 96 of waveguide 70. In addition, reflective surface 72 may be a diffuse reflecting surface that only reflects light having a predetermined wavelength back toward surface 96 of optical cavity 94. Just as with sensing module 20, as the light travels through deflectable member 74 of sensing module 22, the amplitude or another characteristic of the light may be modified in response to the changing optical characteristics of deflectable member 74. The optical characteristics of deflectable member 74 may change as member 74 deflects in response to pressure applied to optical sensing module 22 or in response to vibrations, e.g., from noise. In the example shown in FIG. 6B, the amplitude of the light may be modulated as the light travels through member 74, thereby generating an optical signal that indicates a pressure within patient 12.

Light incident on surface 96, as indicated by arrow 102 in FIG. 6B, is directed toward segment 28 of optically transmissive member 18, which may then guide the light, i.e., the optical signal generated by sensing module 22, to waveguide 62 of optical sensing module 20. Waveguide 62 may then guide the optical signal generated by sensing module 22 to segment 26 of optically transmissive member 18, which may then guide the light to receiver 38 of IMD 14 (FIG. 2).

Figure 7:
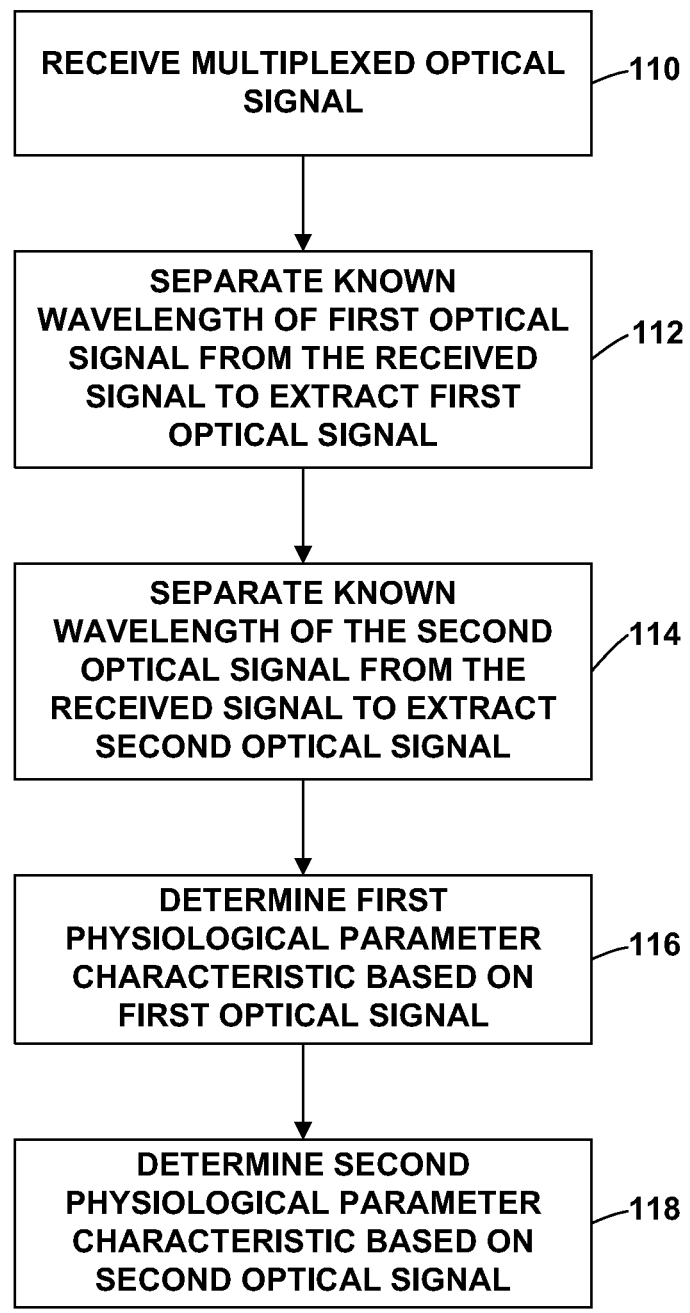
FIG. 7 is a flow diagram illustrating an example technique that may be implemented in order to extract optical signals generated by a plurality of sensing modules from a multiplexed optical signal.

As shown in FIG. 6B, the optical signals generated by sensing modules 20, 22 may traverse through segment 26 of optically transmissive member 18 at substantially the same time. Thus, receiver 38 of IMD 14 (FIG. 2) may received a wavelength division multiplexed signal (or an aggregated signal). FIG. 7 is a flow diagram illustrating a technique that processor 30 of IMD 14 (FIG. 2) may implement in order to extract a first optical signal having a first wavelength generated by sensing module 20 and a second optical signal having a second wavelength generated by sensing module 22 from the multiplexed optical signal received by receiver 38 (FIG. 2). In other examples, a processor of another device may demultiplex the multiplexed optical signal received from optical sensing modules 20, 22 using the technique shown in FIG. 7.

In accordance with the example technique shown in FIG. 7, processor 30 may receive the multiplexed optical signal from receiver 38 of IMD 14 (FIG. 2) (110). Receiver 38 is optically coupled to optically transmissive member 18 via optical coupler 40. The optical signals generated by optical sensing modules 20, 22 may be guided to receiver 38 via optically transmissive member 18. Receiver 38 may then transmit the multiplexed signal to processor 30.

Processor 30 may demultiplex the multiplexed optical signal based on the known wavelengths of the first and second optical signals. As previously indicated, reflective surfaces 64, 72 of optical sensing modules 20, 22, respectively, may act as narrowband filters that only reflect light having a predetermined wavelength back into the respective optical paths 90, 98. Processor 30 may separate out the known wavelength of the first optical signal from the received multiplexed optical signal in order to extract the first optical signal (112). Similarly, processor 30 may separate out the known wavelength of the second optical signal from the multiplexed optical signal in order to extract the second optical signal (114).

Processor 30 may determine a first physiological parameter value of patient 12 based on the first optical signal (116) and determine a second physiological parameter value of patient 12 based on the second optical signal (118). In some examples, optical sensing modules 20, 22 may monitor the same physiological parameters of patient 12, while in other examples, optical sensing modules 20, 22 may monitor different physiological parameters of patient 12. Accordingly, although system 10 including optical sensing modules 20, 22 that are substantially similar are described with respect to FIGS. 4A-6B, in other examples, different types of optical sensing modules may be coupled to a common optically transmissive member.

In other techniques for determining a physiological parameter value of patient 12 based on optical signals from sensing modules 20, 22, processor 30 may use the aggregated optical signals without extracting the separate signal components. For example, in examples in which sensing modules 20, 22 comprise pressure sensors, the aggregated optical signals may indicate the total pressure at the tissue sites occupied by sensing modules 20, 22, without regard to the specific pressure values at the tissue site occupied by sensing module 20 and the specific pressure value at the tissue site occupied by sensing module 22. In examples in which sensing modules 20, 22 comprise pulse oximeters, processor 30 may determine the total relative oxygen saturation level of patient 12 at the tissue sites occupied by sensing modules 20, 22. Thus, system 10 including two or more sensing modules 20, 22 displaced along a length of a common optically transmissive member 18 may be useful for monitoring a larger volume of tissue of patient 12.

FIGS. 8A and 8B are conceptual cross-sectional illustrations of segments 26, 28 of optically transmissive member 18 and example sensing modules 120, 22. Sensing module 120 is similar to sensing module 20 (FIGS. 5A-6B), but includes beam splitter 124, rather than waveguide 62, to direct light toward reflective surface 64 and deflectable member 66. Beam splitter 124 may include any suitable optical device that splits a beam of light into at least two beamlets. For example, beam splitters 124 may each comprise at least two triangular glass prisms that are glued together at their bases. In other examples, beam splitter 124 may comprise a glass plate comprising an aluminum coating or a plate of glass comprising a dielectric optical coating that permits one half of the light incident at about 45 degrees on the mirror to be transmitted through the mirror and the other half of the light to be reflected. As shown in FIGS. 8A and 8B, segments 26, 28 of optically transmissive member 18 may be mechanically and optically coupled to beam splitter 124, e.g., with an adhesive or another suitable technique.

Sensing module 22 is described above with respect to FIGS. 4A-6B, but includes optical waveguide 71 instead of waveguide 70. Waveguide 71 is substantially similar to waveguide 70, but terminates the transmission of light through optically transmissive member 18. That is, waveguide 71 does not transmit light to further sensing modules that are positioned downstream of sensing module 22 in a direction away from housing 24. In some examples, waveguide 71 may direct substantially all of the light received via segment 28 of optically transmissive member 18 toward reflective surface 72 and deflectable member 74.

FIG. 8A illustrates the path of light from light source 36 of IMD 14 (FIG. 2) to optical sensing modules 120, 22. Light may travel through segment 26 of optically transmissive member 18 and into beam splitter 124. Beam splitter 124 is positioned within an optical path between segments 26, 28 of optically transmissive member 18 such that light that propagates through segment 26 exits segment 26 and passes through beam splitter 124 prior to entering segment 28. Beam splitter 124 splits the light introduced into beam splitter 124 into at least a first portion, as indicated by arrow 126, which is directed toward reflective surface 64 and deflectable member 66 of sensing module 120, and a second portion, as indicated by arrow 128, which is directed toward segment 28 of optically transmissive member 18. In this way, beam splitter 124 may enable light source 36 (FIG. 2) of IMD 14 to provide two or more sensing modules 120, 22 with light to sense one or more physiological parameters of patient 12 via a common light transmissive member 18.

Segment 28 of optically transmissive member 18 may guide light into waveguide 70. As previously described, reflective surface 96 of waveguide 70 may direct incident light toward reflective surface 72 and deflectable member 74 of optical sensing module 22. In other examples, such as examples in which one or more additional sensing modules are positioned downstream of sensing module 22 relative to a direction of light flow away from light source 36 (FIG. 2), waveguide 70 may be configured such that at least some light propagates through optical path 98 toward the additional sensors.

FIG. 8B illustrates the path of optical signals generated by optical sensing modules 120, 22 through optically transmissive member 18 and in a direction towards receiver 38 of IMD 14 (FIG. 2). Light that traverses through deflectable member 66 and is reflected by reflective surface 64 of sensing module 120 may be directed toward segment 26 of optically transmissive member 18 by beam splitter 124, as illustrated in FIG. 8B. The light that is reflected by reflective surface 64 may be a first optical signal 130 generated by sensing module 120. As previously discussed with respect to sensor 20 (FIGS. 5A-6B), as deflectable member 66 deflects, the optical properties of deflectable member 66 change. Thus, the amplitude of first optical signal 130 that propagates through deflectable member 66 may be modulated in response to the pressure applied to deflectable member 66. Processor 30 of IMD 14 may determine a pressure value based on the amplitude or other signal characteristic of first optical signal 130 received from sensing module 120.

Light that travels through deflectable member 74 of sensing module 22 may be directed toward segment 28 of optically transmissive member 18 via reflective surface 96 of waveguide 70, as shown in FIG. 8B. The light that traverses through deflectable member 74 may be a second optical signal 132 generated by sensing module 22, where second optical signal 132 indicates a physiological parameter of patient 12. Second optical signal 132 may propagate through beam splitter 124, which does not split the beam when the beam of light travels through beam splitter 124 in a direction toward receiver 38 of IMD 14 (FIG. 2). Second optical signal 132 may then traverse through segment 26 of optically transmissive member 18 to receiver 38. Just as with the first optical signal generated by sensing module 120, processor 30 of IMD 14 may determine a pressure value based on second optical signal 132 received from sensing module 122.

Within segment 26 of optically transmissive member 18, first and second optical signals 130, 132 may combine as the light propagates through segment 26 toward receiver 38 of IMD 14 (FIG. 2). In some examples, reflective surfaces 64, 72 of sensing modules 120, 122 may be diffuse reflective surfaces that reflect light having a predetermined wavelength back toward the beam splitter 124 and reflective surface 96, respectively. In some examples, reflective surfaces 64, 72 may reflect light having different wavelengths. Thus, in some examples, optical signals 130, 132 may have different wavelengths, which may facilitate the extraction of first and second optical signals 130, 132 from the light that is received by receiver 38.

FIGS. 9A and 9B are conceptual cross-sectional illustrations of an implantable sensing system 140 that may be coupled to IMD 14 (FIG. 2). System 140 comprises first optical fiber 142, second optical fiber 144, and sensing modules 148, 150. Optical fibers 142, 144 define a common light transmissive member through which light may propagate from light source 26 of IMD 14 (FIG. 2) to sensing modules 148, 150. Sensing module 148 comprises reflective surface 64, deflectable member 66, and transparent member 68, which are described above with respect to sensing module 20 (FIGS. 4A and 4B). Sensing module 150 comprises reflective surface 72, deflectable member 74, and transparent member 76, which are described above with respect to sensing module 22 (FIGS. 4A and 4B).

Optical fibers 142, 144 are configured to guide light from light source 36 of IMD 14 (FIG. 2) to sensing modules 148, 150. In order to divide the light emitted by light source 36 into different portions that may be directed at each of the sensing modules 148, 150, optical fiber 142 comprises a light deflection member 152 that deflects at least a portion of the light propagating through fiber 142 toward reflective surface 64 and deflectable member 66 of optical sensing module 148. The remaining portion of the light that is not deflected by light deflection member 152 may be introduced into optical fiber 144. In this way, optical fiber 142 comprising light deflection member 152 may define a light dividing member that splits the light from light source 36 into multiple components.

In some examples, light deflection member 152 may comprise a mirror inserted into optical fiber 142, where the mirror comprises a glass plate or titanium dioxide coated with a reflective material. In other examples, light deflection member 152 may comprise one or more prisms, a surface within optical fiber 142 that is coated with a reflective material or an optical waveguide exhibiting total internal reflection. The index of refraction of light deflection member 152 may be selected to help direct light from optical fiber 142 in a particular direction, such as toward reflective surface 64 and deflectable member 66. For example, in examples in which light deflection member 152 comprise a prism or another optical element comprised of glass, the index of refraction of light deflection member 152 may be about 1.3 to about 1.6. As another example, in examples in which light deflection member 152 comprises a waveguide comprised of silicon, the index of refraction of light deflection member 152 may be about 3.5. In some examples, such as examples in which light deflection member 152 comprises a surface of optical fiber 142 coated with a reflective material or a prism, space 154 between optical fibers 142, 144 may be occupied by air.

As FIG. 9A illustrates, light deflection member 152 only directs a portion of the light within optical fiber 142 toward reflective surface 64 and deflectable member 66. The remaining portion of the light may propagate through optical fiber 144 to sensing module 150. Light deflection member 156 may direct the light toward reflective surface 72 and deflectable member 74. Light deflection member 156 may be similar to light deflection member 152. In the example shown in FIGS. 9A and 9B, light deflection member 156 directs substantially all of the light propagating through optical fiber 144 towards reflective surface 72 and deflectable member 74. In other examples, light deflection member 156 may be configured to occlude only part of the optical path through optical fiber 144, such that light deflection member 156 partially reflects the light propagating through optical fiber 144 towards reflective surface 72 and deflectable member 74. This may be useful if additional optical sensing modules are positioned downstream of optical sensing module 150 (relative to a direction of light flow away from light source 36) and optically coupled to optical fiber 144 via another optical fiber.

Just as with optical sensing modules 20, 22, which are described above with respect to FIGS. 4A-6B, sensing modules 148, 150 may each generate an optical signal that varies as a function of the pressure applied to deflectable members 66, 74, respectively. As shown in FIG. 9B, the optical signal generated by sensing module 150 may propagate through optical fiber 144 to optical fiber 142, which may then guide the optical signal to receiver 38 of IMD 14 (FIG. 2). In addition, the optical signal generated by sensing module 148 may propagate through optical fiber 142 to receiver 38. Receiver 38 may receive a multiplexed signal that includes the optical signals generated by sensing modules 148, 152. As described above, processor 30 of IMD 14 may demultiplex the multiplexed signal based on the known wavelengths of the first and second optical signals.

In other examples, instead of or in addition to sensing modules that comprise a deflectable member that deflects and changes position and/or optical properties in response to pressure, temperature, acoustic vibrations or acceleration, a medical system may comprise an optical sensing module that includes a deflectable beam that resonates in response to pressure or acoustic vibrations within patient 12. FIGS. 10A and 10B are conceptual cross-sectional illustrations of an implantable sensing system 160 that may be coupled to IMD 14. FIG. 10A illustrates light traveling through system 160 in a direction away from housing 24 and light source 36 of IMD 14 (FIG. 2), and FIG. 10B illustrates optical signals generated by optical sensing modules 162, 164 propagating in a direction toward housing 24 and receiver 38 of IMD 14 (FIG. 2).

Implantable sensing system 160 comprises light transmissive member 18 comprising segments 26, 28 and waveguides 62, 70, which are described above with respect to FIGS. 4A-6B. As with the previous examples, light transmissive member 18 may be optically coupled to light source 36 and receiver 38 of IMD 14 (FIG. 2). In the example shown in FIGS. 10A and 10B, waveguides 62, 70 are a part of optical sensing modules 162, 164, respectively. Optical sensing module 162 further includes reflective surface 166, resonating beam 168, and transparent member 170. Optical sensing module 164 further includes reflective surface 172, resonating beam 174, and transparent member 176. Reflective surfaces 166, 172 and transparent members 170, 174 may be similar to reflective surface 64 and transparent member 68 of optical sensor 20 (FIGS. 4A-6B).

In some examples, resonating beam 168 and reflective surface 166 may be substantially integral. For example, reflective surface 166 may be defined by a surface of resonating beam 168 that is coated with a reflective material. Similarly, in some examples, resonating beam 174 and reflective surface 172 may be substantially integral.

Resonating beams 168, 174 are adapted to resonate in response to pressure or vibrations within patient 12. Accordingly, the resonance of resonating beams 168, 174 may indicate the relative pressure within patient 12 or indicate cardiac sounds (e.g., a sound associated with a heartbeat). In some examples, the ends of resonating beam 168 may be coupled to a membrane that is fixed to waveguide 62. When the membrane is deflected, e.g., due to changes in pressure, temperature, acoustic waves or acceleration within patient 12, the membrane may increase tension. As a result, resonating beam 168 may also be pulled into tension, e.g., because the ends of beam 168 are coupled to the membrane. The increased tension of beam 168 changes the resonant frequency of beam 168. The changes in resonant frequency of beam 168 or the absolute value of the resonant frequency of beam 168 indicates the pressure, temperature, acoustic waves or acceleration within patient 12.

The changes in the resonant frequency or the absolute value of the resonant frequency may be determined by directing light at beam 168 and determining the frequency of light that reflects off of reflective surface 166 of beam 168. For example, light source 36 of IMD 14 (FIG. 2) may emit light and segment 26 of optically transmissive member 18 may guide the light to waveguide 62. Light incident on surface 86B of waveguide 62 may be directed toward reflective surface 166 and resonating beam 168. As light passes through resonating beam 168, the frequency of the light may be modified. Thus, the frequency of the light that passes through resonating beam 168 and reflected by reflective surface 166 towards waveguide 62 may indicate the relative resonance of beam 168. The vibrating beam 168 will modulate the amplitude and frequency of light that is directed at beam 168.

Receiver 38 may receive the light that has transmitted through beam 168 and processor 30 may determine the relative pressure changes or other physiological parameters of patient 12 based on the frequency of the received light. Processor 30 (FIG. 2) of IMD 14 may determine the frequency of optical signal generated by sensing module 162 using any suitable technique, such as by detecting and counting zero crossings of an alternating current (AC) component of the varying signal amplitude. In this way, properties of the emitted light are changed proportional to the frequency of resonance of the beam 168 and sensing module 162 may generate a first optical signal that indicates a physiological parameter of patient 12.

As previously described, waveguide 62 may divide the light introduced into waveguide 62 into at least two portions. A first portion of the light is directed toward reflective surface 166 and resonating beam 168 of sensing module 162, while another portion is directed toward sensing module 164. In the example shown in FIGS. 10A and 10B, surface 96 of waveguide 71 directs at least a portion of the light propagating through optical pathway 98 in a direction toward reflective surface 172 and resonating beam 174 of sensing module 164. Just as with optical sensing module 162, as light passes through resonating beam 174, the frequency of the light may be modified. Resonating beam 174 may modulate the frequency of the light emitter by light source 36 (FIG. 2) in a substantially similar manner as that described above with respect to resonating beam 168. The frequency-modified light may comprise a second optical signal that indicates a physiological parameter value of patient, such as the relative pressure. As shown in FIG. 10B, reflective surface 172 may direct the second optical signal back toward surface 96 of waveguide 71, which may then direct the light toward optically transmissive member 18 and to receiver 38 of IMD 14 (FIG. 2).

In the example shown in FIGS. 10A and 10B, the light transmitting through optically transmissive member 18 terminates at sensing module 164. However, in other examples, waveguide 70 (FIGS. 5A and 5B) may be substituted for waveguide 71 and additional sensing modules may be positioned downstream of sensing module 164 in a direction away from housing 24 of IMD 14 (i.e., in a direction away from sensing module 162). Waveguide 70 may split the light received via segment 28 of optically transmissive member 18 into at least two portions, whereby a first portion is directed to reflective surface 172 and resonating beam 174 of sensing module 164 and the second portion is directed to another sensing module.

FIGS. 11A and 11B are conceptual cross-sectional illustrations of an implantable sensing system 180 that may be coupled to IMD 14 (FIG. 2). Implantable sensing system 180 may facilitate monitoring of a blood oxygen saturation level of patient 12. In the example shown in FIGS. 11A and 11B, system 180 comprises optically transmissive member 18 including segments 26, 28, and waveguides 62, which are described above with respect to FIGS. 4A-6B and FIG. 8A. System 180 further comprises waveguide 71, which is similar to waveguide 70 of FIGS. 4A-6B, but does not transmit light to additional sensing modules. Waveguides 62, 71 are components of optical sensing modules 182, 184, which may be used to emit light into to tissue of patient 12 and receive light that is reflected by blood of patient 12. In this way, sensing modules 182, 184 may be reflectometer type sensing devices.

Optical sensing modules 182, 184 each generate an optical signal that changes as a function of the hemoglobin of the blood-perfused tissue that is saturated with oxygen as well as the change in hemoglobin concentration in the tissue proximate to the respective modules 182, 184. In some examples, optical sensing modules 182, 184 may sense the changes in volume in an artery associated with contractions of the heart of patient. In this way, the optical signal generated by at least one of the optical sensing modules 182, 184 may be used to detect arterial pulses of patient 12, which may be used to, for example, determine a heart rate of patient 12. In addition, in some examples, the optical signal from at least one of the optical sensing modules 182, 184 may be used to determine a blood oxygen saturation level of patient 12 or tissue perfusion of patient 12. Various hemodynamic characteristics may be derived from relative changes in a blood oxygen saturation level of a patient, such as relative changes in the blood pressure of the patient.

In the example shown in FIGS. 11A and 11B, optical sensing modules 182, 184 are optically coupled to a common light source 36 and receiver 38 via optically transmissive member 18. Light source 36 may emit light at a particular wavelength, and the light may be guided to tissue of patient 12 via optically transmissive member 18 and waveguides 62, 71. As FIG. 11A illustrates, light may traverse through segment 26 of optically transmissive member 18 in a direction away from light source 36 of IMD 14 (FIG. 2), as indicated by arrow 92. Waveguide 62 of optical sensing module 182 may divide the light that propagates through optical pathway 90, which extends between segments 26, 28 of optically transmissive member 18. Light incident on surface 86B of waveguide 62 may be directed toward tissue proximate to waveguide 62, as indicated by arrow 186. The emitted light may scatter through blood-perfused tissue of patient 12 proximate to optical sensing module 182.

As FIG. 11B illustrates, waveguide 62 is configured to received emitted light that is reflected by blood of patient 12 toward the waveguide 62, as indicated by arrow 188. Surface 86B of waveguide 62 may direct the reflected light 188 toward segment 26 of optically transmissive member 18. The received light 188 may be transmitted to receiver 38 via optically transmissive member 18. In some examples, receiver 38 may generate an electrical signal that indicates the intensity of light received by receiver 38. In this way, in some examples, receiver 38 may be configured to sense light that is emitted by light source 36 and reflected by blood of patient 12. In some examples, light source 36 may comprise at least two light sources that emit light at different wavelengths (e.g., red light wavelengths and IR light wavelengths, which are described above), and, in some cases, receiver 38 may comprise a photodetector that is sensitive to a broadband of light or at least two photodetectors that are sensitive to different wavelengths of light.

The optical properties of blood-perfused tissue may change depending upon the relative amounts of oxygenated and deoxygenated hemoglobin due, at least in part, to their different optical absorption spectra. That is, the oxygen saturation level of the patient's blood may affect the amount of light that is absorbed by a blood mass and the amount of light that is reflected back to optical sensing module 182. Accordingly, the intensity of the light 188 (e.g., as indicated by the amplitude of the optical signal) emitted by light source 36, reflected by blood, and received by sensing module 182 may change in response to the amount of oxygenated and deoxygenated hemoglobin in the tissue proximate to optical sensing module 182. Thus, light 188 received by optical sensing module 182 may comprise an optical signal that indicates the relative amounts of oxygenated and deoxygenated hemoglobin in the tissue proximate to optical sensing module 182. Processor 30 may detect a pulsatile component (e.g., an arterial pulse associated with a heartbeat) of a cardiac cycle of patient 12 or the relative blood oxygen saturation level of patient 12 based on the intensity of optical signal generated by optical sensing module 182.

Optical sensing module 184 may generate an optical signal that indicates a blood oxygen saturation level of patient 12 in a substantially similar manner as optical sensing module 182. As previously indicated, waveguide 62 may divide light emitted by light source 36 into at least two portions. A first portion may be directed toward tissue of patient 12 proximate sensing module 182, while a second portion may propagate through segment 28 of optically transmissive member 28 toward waveguide 71 of sensing module 184. In some examples, waveguide 71 may divide the light within optical pathway 98 into multiple components, whereby one portion of the light is directed toward tissue of patient 12 proximate sensing module 184 (e.g., proximate optical cavity 94 of waveguide 71) and another portion is directed toward another sensing module. In other examples, waveguide 71 may direct substantially all of the light within optical pathway 98 toward tissue of patient 12 proximate sensing module 184.

Light incident on surface 96 of waveguide 71 may deflect or reflect toward tissue of patient 12 proximate optical cavity 94, as indicated by arrow 190. The light may scatter through the tissue. The light reflected by blood of patient 12 and incident on surface 96 of waveguide 71, as indicated by arrow 192, may be directed toward segment 28 of optically transmissive member 18. The amount of oxygenated and deoxygenated hemoglobin within tissue proximate to optical cavity 94 may modulate the intensity of the light that is incident on surface 96. Thus, the light reflected by blood of patient 12 and incident on surface 96 may comprise an optical signal generated by sensing module 184, where the optical signal indicates a blood oxygen saturation level of patient 12 or another hemodynamic characteristic of patient 12.

The optical signals 188, 192 generated by sensing modules 182, 184 propagate through a common optically transmissive member 18 to receiver 38. In some examples, processor 30 of IMD 14 may determine the relative changes in blood oxygen saturation level of patient 12 based on the signals from both sensing modules 182, 184 without regard to the specific intensity of optical signal 188 generated by sensing module 182 and the specific intensity of optical signal 192 generated by sensing module 184. System 180 comprising at least two optical sensing modules 182, 184 that sense a blood oxygen saturation level of patient 12 and are distributed along a length of a common optically transmissive member 18 may be useful for monitoring the blood oxygen saturation level of patient 12 or another hemodynamic characteristic (e.g., tissue perfusion) of a larger volume of tissue compared to a single sensing module implanted within patient 12.

In some examples, processor 30 of IMD 14 (FIG. 2) may distinguish between the optical signals generated by sensing modules 182, 184 to determine the blood oxygen saturation level of patient 12 at the specific tissue sites proximate to sensing modules 182, 184. In some examples, optical signals 188, 192 may comprise different wavelengths, and processor 30 may demultiplex the signal received from optically transmissive member 18 based on the known wavelengths of optical signals 188, 192. In order to determine the blood oxygen saturation level of patient 12, light source 36 (FIG. 2) may sequentially emit broadband light in the red light spectrum and broadband light in the IR light spectrum. Optical signals 188, 192 generated by sensing modules 182, 184 may each have a wavelength of light within the broadband red light or the broadband IR light emitted by light source 36.

Optical sensing modules 182, 184 may each comprise an optical filter to filter a particular wavelength of light from the light emitted by light source 36. In some examples, the optical filter may comprise an optical material positioned within optical cavity 184 of waveguide 62 or proximate cavity 184. The optical filter may comprise, for example, glass, resin plastics, a polymer (e.g., polyester or polycarbonate), or the like.

In the example shown in FIGS. 11A and 11B, the light transmitting through optically transmissive member 18 terminates at sensing module 184. However, in other examples, waveguide 70 (FIGS. 5A and 5B) may be substituted for waveguide 71 and additional sensing modules may be positioned downstream of sensing module 184 in a direction away from housing 24 of IMD 14 (i.e., in a direction away from sensing module 182). As previously described, waveguide 70 may split the light received via segment 28 of optically transmissive member 18 into at least two portions, whereby a first portion is directed to tissue proximate sensing module 184 and the second portion is directed to another sensing module, which may or may not be another reflectometer type sensing device.

Figure 12:
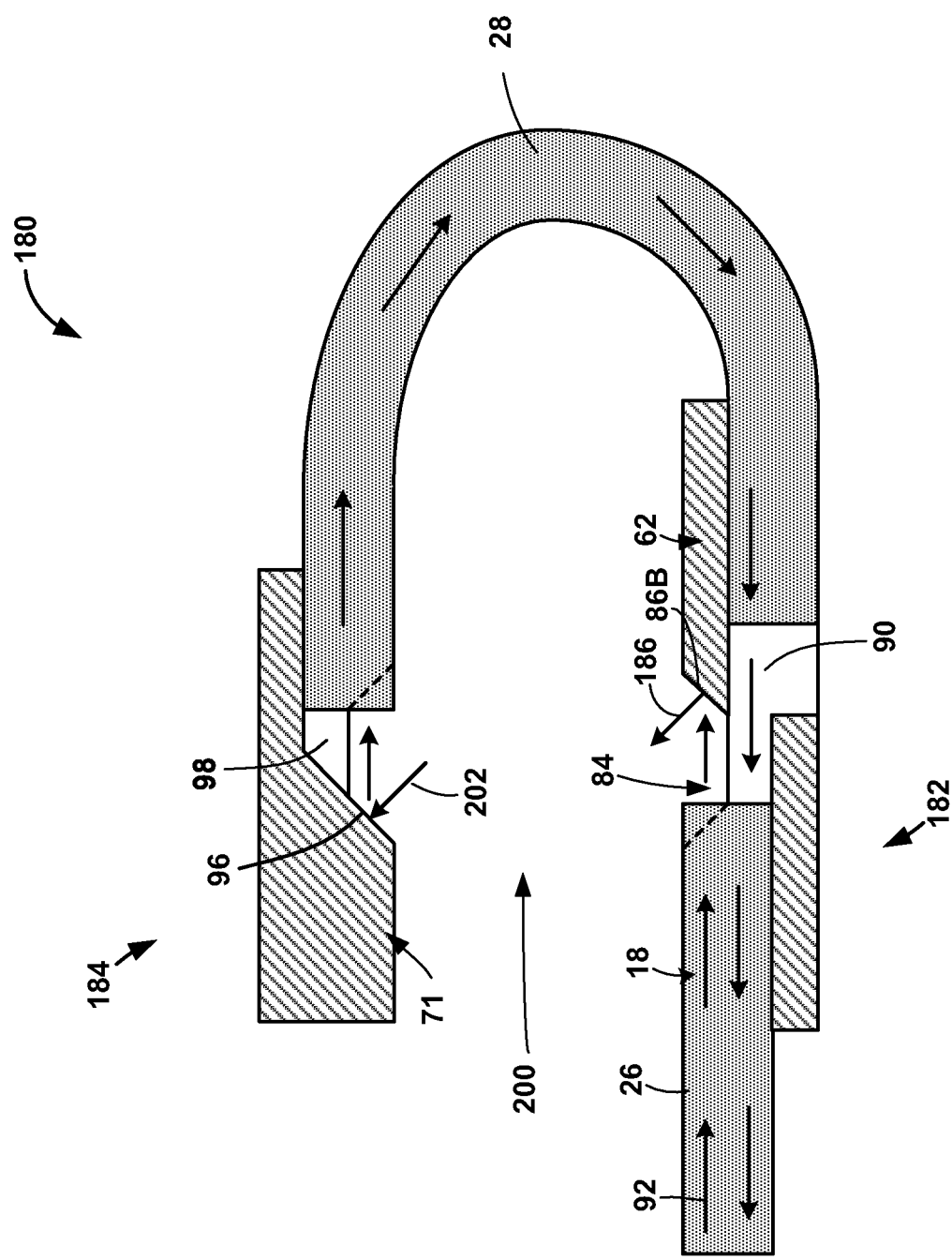
FIGS. 12-13B are conceptual cross-sectional illustrations of example configurations of the optically transmissive member and example sensing modules shown in FIGS. 11A and 11B.

FIG. 12 is an example of another configuration of system 180. During implantation of system 180 within patient 12, a clinician may arrange optically transmissive member 18 such that blood-perfused tissue of patient 12 is positioned in space 200 between sensing modules 182, 184. Blood-perfused tissue may comprise, for example, tissue comprising a blood mass (e.g., blood cells in a blood vessel) of patient 12. In the example shown in FIG. 12, segment 28 of optically transmissive member 18 may comprise a curvilinear shape or may be substantially flexible to enable the clinician to manipulate the position of sensing modules 182, 184 relative to each other.

The arrangement between sensing modules 182, 184 shown in FIG. 12 may define a transmissive-type reflectometer, in which sensing modules 182, 184 sense light that is emitted by light source 36 (FIG. 2) and transmitted through tissue within space 200 between sensing modules 182, 184. Receiver 38 may be configured to generate an electrical signal indicative of an intensity of light emitted by the light source 36, transmitted through tissue of patient, and collected by at least one of the sensing modules 182, 184. As described above, various hemodynamic characteristics of patient 12 may be determined based on the electrical signal indicative of the intensity of light emitted by light source 36, transmitted through tissue, and collected by sensing module 184.

In one example, waveguide 62 of sensing module 182 may direct substantially all of the light emitted by light source 36 toward reflective surface 86B and into tissue of patient 12. The light may transmit through tissue within space 200 between sensing modules 182, 184, and light incident on reflective surface 96 of waveguide 71, as indicated by arrow 202, may be reflect off of surface 96 and into waveguide 71. The light 202 may then transmit through segment 28 of optically transmissive member 18, which may guide the received light 200 to receiver 38, which may generate an electrical signal indicative of an intensity of light sensed by sensing module 184.

The light 92 emitted by light source 36 and the light 202 collected by sensing module 184 may traverse through optically transmissive member 18 at different times. For example, processor 30 may control light source 36 to stop emitting light for a short period of time following the emission of light in order to permit the light 202 collected by sensing module 184 to propagate through optically transmissive member 18 toward receiver 38 (FIG. 2).

Figure 13A:
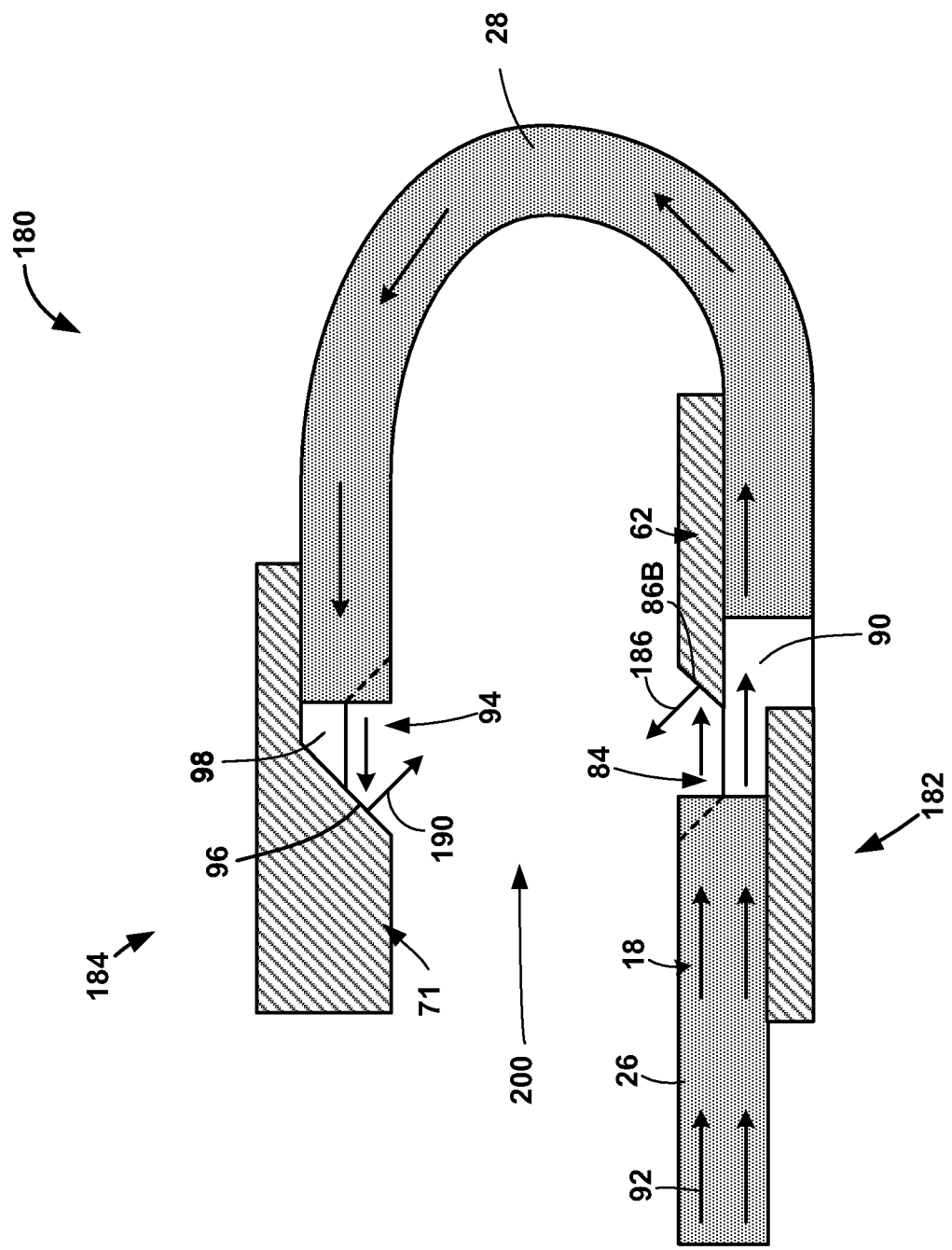
Figure 13B:
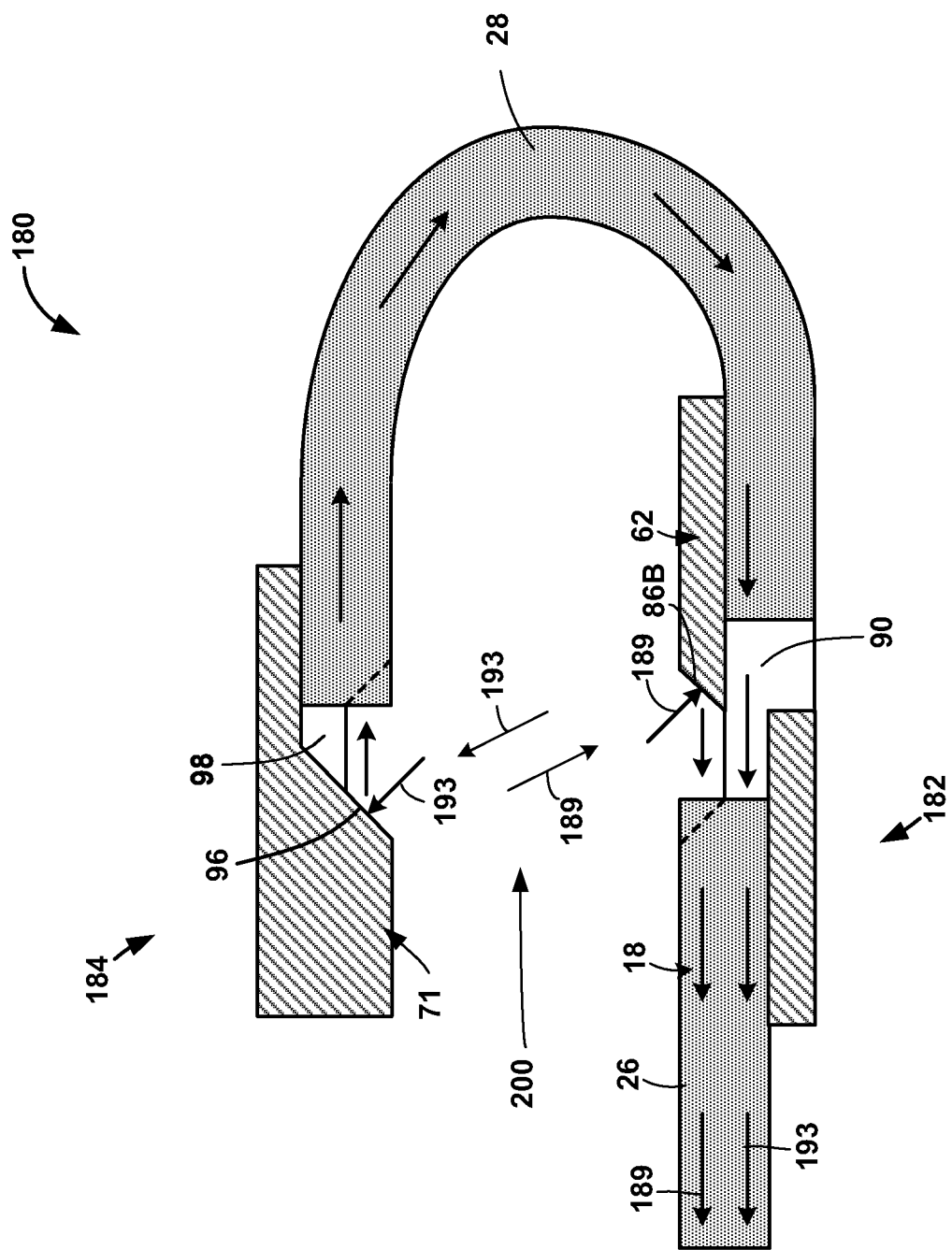

FIGS. 13A and 13B illustrate another example configuration of system 180. Rather than emitting light at one sensing module 182 and detecting light at another sensing module 184, both sensing modules 182, 184 may emit light and detect light that is transmitted through tissue within space 200. For example, as conceptually shown in FIG. 13A, processor 30 may control light source 36 (FIG. 2) to emit light, which is then guided to optical sensing modules 182, 184 by optically transmissive member 18. As previously described, waveguide 62 may split the light 92 into a first portion, which is directed toward tissue proximate to waveguide 62, as indicated by arrow 186, and a second portion, which propagates toward segment 28 of optically transmissive member 18. The emitted light that is directed toward waveguide 62 may reflect off of surface 86B and transmit through blood-perfused tissue of patient 12 within space 200. The second portion of light split by waveguide 62 may propagate through segment 28 of optically transmissive member 18 toward waveguide 71 of sensing module 184. Light incident on surface 96 of waveguide 71 may deflect or reflect toward tissue of patient 12 proximate optical cavity 94, as indicated by arrow 190 in FIG. 13A. The light may scatter through the tissue within space 200.

As FIG. 13B illustrates, waveguide 62 is configured to receive emitted light that is introduced into tissue of patient 12 by sensing module 184 and transmitted through blood-perfused tissue within space 200, as indicated by arrow 189. That is, waveguide 62 may collect light 189 that is released into tissue via waveguide 71 and transmitted through tissue from sensing module 184 to sensing module 182. The generally positioning of sensing modules 182, 184 opposite each other may facilitate the transmission of light from sensing module 182 to sensing module 184. However, sensing modules 182, 184 do not need to be directly opposed one another because light is scattered through the tissue within space 200. Due to the scattering properties of the tissue, light may transmit from sensing module 184 through tissue and to sensing module 184 despite sensing modules 182, 184 not being directly opposing each other.

Surface 86B of waveguide 62 may direct the collected light 189 toward segment 26 of optically transmissive member 18. The received light 189 may be transmitted to receiver 38 via optically transmissive member 18. In some examples, receiver 38 may generate an electrical signal that indicates the intensity of light received by receiver 38, which may indicate the relative amounts of oxygenated and deoxygenated hemoglobin in the tissue within space 200 between sensing modules 182, 184. In this way, in some examples, receiver 38 may be configured to sense light that is emitted by light source 36 and transmitted through blood perfused tissue of patient 12.

Waveguide 71 is configured to collect light 193 that is released into tissue via sensing module 182 and transmitted through tissue within space 200 in a direction from sensing module 182 to sensing module 184. Surface 96 of waveguide 71 may direct the collected light 193 toward segment 28 of optically transmissive member 18, and the light may propagate through optically transmissive member 18 (e.g., segments 26, 28) and waveguide 62 to receiver 38. In some examples, receiver 38 may generate an electrical signal that indicates the intensity of light 193 received by receiver 38, which may indicate the relative amounts of oxygenated and deoxygenated hemoglobin in the tissue within space 200 between sensing modules 182, 184.

As shown in FIG. 13B, the optical signals 189, 193 generated by sensing modules 182, 184, respectively, may propagate through a common optically transmissive member 18 to receiver 38. In some examples, optical signals 189, 193 may have different properties, e.g., different wavelengths, in order to permit processor 30 to demultiplex signals 189, 193.

The techniques described in this disclosure, including those attributed to IMD 14, external device 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

In other examples, the techniques described as being performed by processor 30 of IMD 14 may be performed in whole or in part by processor 50 of external device 16 or another device. For example, processor 50 of external device 16 may receive optical signals generated by optical sensing modules 20, 22 or an electrical signal generated by receiver 38 and determine a physiological parameter value of patient 12 based on the optical signals and/or electrical signals.

Various examples of medical systems and techniques have been described. These and other examples are within the scope of the following claims.

The invention claimed is:

1. An implantable medical system comprising:
a light source configured to emit light;
an implantable optically transmissive member comprising a waveguide comprising an optical cavity, a first segment and a second segment, the first segment optically coupled to the light source and configured to propagate the light emitted by the light source to a distal end of the first segment, the distal end of the first segment received at a first end of the waveguide so that the light emitted by the light source and propagated from the light source through the first segment toward the distal end of the first segment exits the distal end of the first segment and is received at the optical cavity, the second segment having a proximal end received at a second side of the waveguide, the first side of the waveguide separated from the second side of the waveguide by the optical cavity, wherein the first segment is physically separated from the second segment by the optical cavity and is optically coupled to the second segment through at least one optical path formed through the optical cavity:
a light dividing member positioned within the optical cavity and configured to divide the light from the light source received at the optical cavity through the first segment into at least a first portion and a second portion, wherein the light dividing member comprises at least one surface within the optical cavity that occludes a first portion of the optical cavity and is configured to direct the first portion of the light, and wherein a second portion of the optical cavity is unobstructed by the light dividing member, the second portion of the optical cavity comprising the at least one optical path between the first segment and the second segment through the optical cavity for the second portion of light:
a first sensing module optically coupled to the first and second segments of the optically transmissive member, the first sensing module configured to receive the first portion of light and generate a first optical signal; and
a second sensing module optically coupled to the second segment of the optically transmissive member, the second sensing module configured to receive only the second portion of the light and generate a second optical signal,
wherein the first sensing module and the second sensing module are configured to modulate one or more properties of the first and second portions of light as a function of one or more physiological parameters of a patient.

2. The implantable medical system of claim 1, wherein the light dividing member comprises a first light dividing member, the system further comprising a second light dividing member that divides the second portion of the light into at least a third portion and at least a fourth portion, wherein the second sensing module is configured to receive the third portion of the light.

3. The implantable medical system of claim 2, further comprising a third sensing module optically coupled to the optically transmissive member, wherein the optically transmissive member is configured to guide the fourth portion of the light toward the third sensing module.

4. The implantable medical system of claim 1, further comprising a receiver configured to receive the first optical signal and the second optical signal and generate electrical signals based on the first and second optical signals, and a processor configured to determine a physiological parameter value of the patient based on at least one of the first or second optical signals.

5. The implantable medical system of claim 1, wherein the at least one surface of the light dividing member further comprises a reflective surface configured to direct the first portion of the light from the optical cavity to the first sensing module.

6. The implantable medical system of claim 1, wherein the first sensing module comprises a first light filter configured to filter a first wavelength of light from the first portion of the light, wherein the first optical signal comprises the first wavelength of light, and wherein the second sensing module comprises a second light filter configured to filter a second wavelength of light from the second portion of the light, wherein the second optical signal comprises the second wavelength of light.

7. The implantable medical system of claim 6, wherein the first and second wavelengths of light are the same.

8. The implantable medical system of claim 6, wherein the first and second wavelengths of light are different.

9. The implantable medical system of claim 6, wherein at least one of the first or second light filters comprises a diffuse reflective surface.

10. The implantable medical system of claim 6, wherein at least one of the first or second light filters comprises an optical material disposed within the first or second sensing modules.

11. The implantable medical system of claim 1, further comprising a receiver configured to receive a third optical signal and extract the first and second optical signals from the third optical signal.

12. The implantable medical system of claim 11, wherein the first and second optical signals comprise different wavelengths of light, wherein the receiver is configured to extract the first and second optical signals from the third optical signal based on known wavelengths of light of the first and second optical signals.

13. The implantable medical system of claim 5, wherein the reflective surface comprises a gold or aluminum surface.

14. The implantable medical system of claim 1, wherein the first sensing module, the second sensing module, or both the first and second sensing modules comprises a sensing element that modulates at least one of an amplitude, wavelength, phase, frequency or velocity of the light to generate at least one of the first or second optical signals.

15. The implantable medical system of claim 14, wherein the sensing element comprises a deflectable member, a resonating beam, or a combination of the deflectable member and the resonating beam.

16. The implantable medical system of claim 1, wherein the first sensing module comprises a first optical resonance sensor configured to modulate a frequency of the first portion of the light, the second sensing module comprises a second optical resonance sensor configured to modulate a frequency of the second portion of the light, or both the first sensing module comprises the first optical resonance sensor and the second sensing module comprises the second optical resonance sensor.

17. The implantable medical system of claim 1, wherein the light dividing member is configured to direct the first portion of the light toward tissue of the patient and receive light that is emitted by the light source and reflected by blood of the patient within the tissue, the received light comprising the first optical signal, wherein the first optical signal is indicative of a blood oxygen saturation level of the patient.

18. The implantable medical system of claim 1, wherein the first and second sensing modules are distributed along a length of the optically transmissive member.

19. The implantable medical system of claim 1, wherein the first sensing module is optically coupled to the first and second segments and the second sensing module is optically coupled to the second segment.

20. The implantable medical system of claim 1, wherein the first and second optical signals change as a function of different physiological parameters.

21. The implantable medical system of claim 1, wherein the one or more physiological parameters comprise one or more of: a blood pressure, a blood oxygen saturation level, a temperature, a parameter indicative of patient movement, acoustic vibrations, or cardiac activity.

22. A method comprising:
controlling a light source within a medical device housing to emit light; transmitting the light through an optically transmissive member to first and second sensing modules optically coupled to the optically transmissive member, wherein the implantable optically transmissive member comprises a waveguide comprising an optical cavity, a first segment and a second segment, the first segment optically coupled to the light source and configured to propagate the light emitted by the light source to a distal end of the first segment, the distal end of the first segment received at first end of the waveguide so that the light emitted by the light source and propagated through the first segment toward the distal end of the first segment exits the distal end of the first segment and is received at the optical cavity, the second segment having a proximal end received at a second side of the waveguide, the first side of the waveguide separated from the second side of the waveguide by the optical cavity, wherein the first segment is physically separated from the second segment by the optical cavity and is optically coupled to the second segment through at least one optical path formed through the optical cavity, and wherein the first sensing module is optically coupled to the first and second segments of the optically transmissive member, the second sensing module is optically coupled to the second segment of the optically transmissive member, the light emitted by the light source propagates through the first segment to the first sensing module and through the first and second segments to the second sensing module, the first sensing module comprises a light dividing member positioned within the optical cavity that divides the light received at the optical cavity through the first segment into at least a first portion and a second portion, wherein the light dividing member comprises at least one surface within the optical cavity that occludes a first portion of the optical cavity and is configured to direct the first portion of the light, and wherein a second portion of the optical cavity is unobstructed by the light dividing member, the second portion of the optical cavity comprising the at least one optical path between the first segment and the second segment through the optical cavity for the second portion of light, directing, using the light dividing member and the optical cavity, the light exiting the distal end of the first segment so that the first sensing module receives the first portion of the light, and the optically transmissive member guides the second portion of the light toward the second sensing module, wherein the first and second sensing modules are configured to modulate a property of the first and second portions of light as a function of one or more physiological parameters of a patient;

receiving a first optical signal generated by the first sensing module based on the first portion of the light;

receiving a second optical signal generated by the second sensing module based on the second portion of the light; and determining a physiological parameter value of a patient based on at least one of the first or second optical signals.

23. The method of claim 22, further comprising receiving a third optical signal via the optically transmissive member and extracting the first and second optical signals from the third optical signal.

24. The method of claim 23, wherein the first and second optical signals comprise different wavelengths of light, wherein extracting the first and second optical signals from the third optical signal comprises extracting the first and second optical signals from the third optical signal based on known wavelengths of light of the first and second optical signals.

25. The method of claim 22, wherein the first and second optical signals change as a function of different physiological parameters.

26. The method of claim 22, wherein the one or more physiological parameters comprise one or more of a blood pressure, a blood oxygen saturation level, a temperature, or a parameter indicative of patient movement, acoustic vibrations, or cardiac activity.

* * * * *